US006969450B2

(12) United States Patent
Taniike et al.

(10) Patent No.: US 6,969,450 B2
(45) Date of Patent: Nov. 29, 2005

(54) BIOSENSOR AND MEASURING APPARATUS FOR BIOSENSOR

(75) Inventors: Yuko Taniike, Osaka (JP); Mariko Miyashita, Nishinomiya (JP); Shin Ikeda, Katano (JP); Toshihiko Yoshioka, Hirakata (JP); Yoshinobu Tokuno, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 123 days.

(21) Appl. No.: 10/616,305

(22) Filed: Jul. 10, 2003

(65) Prior Publication Data

US 2005/0224345 A1    Oct. 13, 2005

(30) Foreign Application Priority Data

Jul. 18, 2002    (JP) ................. 2002-209062

(51) Int. Cl.[7] ................................. C12M 1/00
(52) U.S. Cl. ................. 204/403.01; 204/403.02; 204/403.04; 204/403.14
(58) Field of Search ............ 204/403.01–403.15; 205/777.5–778

(56) References Cited

U.S. PATENT DOCUMENTS

| | | | | |
|---|---|---|---|---|
| 5,096,669 A | * | 3/1992 | Lauks et al. | 204/403.02 |
| 5,266,179 A | | 11/1993 | Nanakai et al. | |
| 5,320,732 A | | 6/1994 | Nankai et al. | |
| 5,821,399 A | * | 10/1998 | Zelin | 73/1.02 |
| 6,071,391 A | * | 6/2000 | Gotoh et al. | 204/403.05 |
| 6,495,104 B1 | * | 12/2002 | Unno et al. | 422/68.1 |
| 6,616,819 B1 | * | 9/2003 | Liamos et al. | 204/403.02 |

FOREIGN PATENT DOCUMENTS

| | | |
|---|---|---|
| EP | 0 964 059 A2 | 12/1999 |
| EP | 1 304 566 A1 | 4/2003 |
| JP | 3-202764 | 9/1991 |
| JP | 09-159642 | * 6/1997 ......... G01N 27/28 |
| JP | 9-159642 | 6/1997 |
| JP | 11-352093 | 12/1999 |
| WO | WO 01/33216 A1 | 5/2001 |
| WO | WO 01/71328 A1 | 9/2001 |
| WO | WO 02/00918 | 1/2002 |
| WO | WO 02/08743 A1 | 1/2002 |

* cited by examiner

*Primary Examiner*—Nam Nguyen
*Assistant Examiner*—Jeffrey T. Barton
(74) *Attorney, Agent, or Firm*—McDermott Will & Emery LLP

(57) ABSTRACT

In biosensor system 1, biosensor 2 is mounted in measuring apparatus 3 for quantifying or detecting existence of a targeted substrate in a sample solution. Mounting end portion 20 of biosensor 2 to be mounted in measuring apparatus 3 has an extension of one base plate in the length direction, and further extensions of the other base plate in the width direction. Sensor mounting portion 30 of measuring apparatus 3 has a shape matching up with the shape of mounting end portion 20. Thereby wrong insertion of biosensor 2 in measuring apparatus 3 can be prevented.

Further, varying shapes of plural biosensors 5 and 6 to have a common part and a non-common part, such biosensors can be handily measured by one measuring apparatus 7.

14 Claims, 14 Drawing Sheets

BIOSENSOR AND MEASURING APPARATUS FOR BIOSENSOR

BACKGROUND OF THE INVENTION

The present invention relates to a biosensor and a measuring apparatus for a biosensor for quantifying and/or detecting existence of a substrate contained in a sample solution.

A biosensor is such a sensor that uses, for a molecule discrimination device, fundamental biological elements such as microbes, enzymes, antibodies, DNAs (deoxyribonucleic acids) and RNAs (ribonucleic acids). More specifically, a biosensor can quantify or detect existence of a substrate contained in a sample solution by utilizing a reaction generated when a substrate is recognized or contacted by a fundamental biological element, for example, such reaction as oxygen consumption by microbial respiration, light emission or enzyme reaction.

Among various biosensors, the commercialization of enzyme sensors, which quantify or detect existence of substrates by using an enzyme and reacting the enzyme with a targeted substrate, has been advanced. For example, enzyme sensors to be used for such targeted substrates as glucose, lactic acid, cholesterol and amino acid are called, e.g., glucose sensor, cholesterol sensor and so forth on the basis of the names of the targeted substrates, and are used for medical measurements, food industry and so on.

According to a measuring system using such enzyme sensor, an electron mediator is reduced by electrons generated, e.g., by the reaction of a certain material (substrate) contained in a sample solution with e.g. an enzyme. The amount of reduction of the electron mediator is electrochemically measured, thereby quantifying the substrate contained in the sample solution.

One of performance capabilities that such biosensor is required to have is capability of conducting the measurement with high accuracy even if the sample solution is in a trace amount. For example, when a patient of diabetes uses a glucose sensor, the sample solution is often a blood taken from the patient. In order to decrease the burden of the patient, it is desired that the amount of blood to be taken from the patient be as small as possible.

Thus, as a biosensor having a capability of conducting measurement even with a trace amount of sample solution, a biosensor of electrode-opposed type is proposed as disclosed in Japanese Laid-open Patent Publication Hei 11-352093. In such proposed biosensor, a working electrode placed on a base plate for the working electrode and a counter electrode placed on a base plate for the counter electrode are opposed to each other with a space therebetween to which a sample solution is supplied. Accordingly, when a voltage is applied between the working electrode and the counter electrode, with the sample solution being supplied to the space, charge transfer between the working electrode and the counter electrode well progresses. Accordingly, measurement with high accuracy becomes possible even with a trace amount of the sample solution.

However, the biosensor of electrode-opposed type has electric connection terminals (which are electrically connected to a driving power supply in a measuring apparatus for a biosensor when the sensor is inserted or mounted in the apparatus) placed on topside and downside of a pair of base plates, respectively, without any specific design. Accordingly, it is difficult for a user to discriminate, e.g. visually, between the topside and downside of the biosensor. Therefore, there is a possibility that the user may insert the biosensor upside down, making a mistake in the top-down side matching of the biosensor with respect to the apparatus. With such wrong insertion of the biosensor, correct measurement cannot be expected.

It is further desired that one measuring apparatus can be used for measuring biosensors corresponding to plural targeted substrates handily without causing wrong insertion of the biosensors. However, it cannot be realized by a conventional biosensor or a combination of a conventional biosensor and a conventional measuring apparatus for a biosensor.

BRIEF SUMMARY OF THE INVENTION

Thus, an object of the present invention is to provide a biosensor and a measuring apparatus for a biosensor, in which wrong insertion of the biosensor into the measuring apparatus by a user can be prevented.

Another object of the present invention is to provide a measuring apparatus for a biosensor, which apparatus can be handily used for measuring plural biosensors corresponding to plural targeted substrates without causing wrong insertion of the biosensors.

For solving the above-described problems and achieving the objects, a biosensor according a first aspect of the present invention comprises: a first insulating base plate comprising a first electrode provided thereon, and a second insulating base plate comprising a second electrode provided thereon, the first and the second electrodes being opposed to each other; and a first lead provided on the first base plate and connected to the first electrode, and a second lead provided on the second base plate and connected to the second electrode, wherein the first base plate comprises a first extension portion which extends in a length direction of the first base plate from a position corresponding to an end of the second base plate in its length direction, and has at least a part of the first lead exposed to outside, and wherein the second base plate comprises a second extension portion which extends in a width direction of the second base plate from a position corresponding to an end of the first base plate in its width direction, and has at least a part of the second lead exposed to outside.

An advantage of such biosensor is in that wrong insertion of the biosensor by a user into a measuring apparatus can be easily prevented.

Such biosensor can further be so structured that the second base plate comprises two of the second extension portions, one of which extends in the width direction of the second base plate from the position corresponding to the end of the first base plate in its width direction, and the other of which extends in the width direction of the second base plate from a further position corresponding to a further end of the first base plate in its width direction.

The biosensor having such structure has an advantage in that the second base plate can have extension portions extending to both width directions, so that the biosensor can have good mechanical balance between both sides of the biosensor with respect to the centerline in the length direction of the biosensor.

The biosensor can further comprise: a sample solution supply path for supplying a sample solution containing a plurality of substrates in a manner that sample solution contacts the first electrode and the second electrode; and a reagent which can react with at least one specific substrate in the plurality of substrates, wherein the first base plate or the second base plate has a shape having a common part and a non-common part, the non-common part having a specific shape corresponding to the specific substrate. Such biosensor can handily be adapted to a targeted substrate, and can also be handily adapted to a measuring apparatus for measuring plural biosensors corresponding to plural targeted substrates without causing an operational error.

Furthermore, the biosensor can be so structured that the first extension portion of the first base plate or the second extension portion of the second base plate is positioned at a specific position (of the first base plate or the second base plate) corresponding to the specific substrate. For example, the structure of the biosensor can be such that the specific position of the second extension portion of the second base plate is left position or right position, corresponding to the specific substrate, in the length direction of the second base plate, namely with respect to the centerline on the second base plate in its length direction.

By such structure, the biosensor can handily be adapted to a targeted substrate.

Further, in the biosensor, the plurality of substrates can be so selected to be glucose and lactic acid. Thereby, the biosensor can handily be adapted to glucose measurement and lactic acid measurement that are most desired by biosensor users.

A measuring apparatus for a biosensor according to a further aspect of the present invention comprises a sensor mounting portion for mounting the biosensor, wherein the sensor mounting portion comprises segmental portions respectively provided therein at positions corresponding to the common part and the non-common part of the first base plate or the second base plate, and wherein when the biosensor is mounted in the sensor mounting portion, the specific substrate in the biosensor is discriminated by the position of the segmental portion of the sensor mounting portion corresponding to the non-common part of the first base plate or the second base plate.

The measuring apparatus can further be so structured that the sensor mounting portion comprises an integral fitting space for having the sensor fitted thereto, which space comprises: a first region corresponding to the common part of the shape of the first base plate or the second base plate; and a second region corresponding to the non-common part of the shape of the first base plate or the second base plate.

The measuring apparatus can also be so structured that it further comprises: a first electric connection terminal positioned therein for contact with the first region of the integral fitting space; and a plurality of second electric connection terminals positioned therein for contact with the second region of the integral fitting space, wherein when the biosensor is mounted in the sensor mounting portion, one of the first and the second leads is connected to the first electric connection terminal, and the other of the first and the second leads is connected to one of the plurality of second electric connection terminals, and wherein the specific substrate in the biosensor is discriminated by the one of the plurality of second electric connection terminals to which the other of the first and the second leads is connected.

An advantage of these measuring apparatuses is that a single measuring apparatus can be adapted for measuring plural different biosensors respectively comprising specific or different substrates without causing an operational error.

A measuring apparatus for a biosensor, according to a further aspect of the present invention, comprises a sensor mounting portion for mounting therein a biosensor comprising a first base plate and a second base plate, wherein the sensor mounting portion comprises: a first sensor mounting segmental portion corresponding to the first base plate of the biosensor; and a second sensor mounting segmental portion corresponding to the second base plate of the biosensor, and wherein the first sensor mounting segmental portion has a width different from that of the second sensor mounting segmental portion.

The measuring apparatus can further be so structured that the first base plate of the biosensor comprises a first electrode and a first lead provided thereon, the first lead being connected to the first electrode; the second base plate comprises a second electrode and a second lead provided thereon, the second lead being connected to the second electrode; and the first and the second electrodes are opposed to each other, wherein the first base plate comprises a first extension portion which extends in a length direction of the first base plate from a position corresponding to an end of the second base plate in its length direction, and has at least a part of the first lead exposed to outside, and wherein the second base plate comprises a second extension portion which extends in a width direction of the second base plate from a position corresponding to an end of the first base plate in its width direction, and has at least a part of the second lead exposed to outside.

An advantage of such measuring apparatuses is that wrong insertion of the biosensor, by a user, into the measuring apparatus can be prevented.

Such measuring apparatus can also be so structured that it further comprises: a first electric connection terminal to be connected with the exposed part of the first lead, and a second electric connection terminal to be connected with the exposed part of the second lead of the biosensor when the biosensor is mounted in the sensor mounting portion; and a driving power supply coupled to the first and the second electric connection terminals for applying a voltage to the first and the electrodes of the biosensor through the first and the second electric connection terminals.

An advantage of such structure of the measuring apparatus is that a voltage necessary for the measurement can handily be applied to a sample solution in the biosensor having a targeted substrate.

Such measuring apparatus can still further be so structured that it further comprises: a signal processor to be operatively coupled to the first electrode and the second electrode of the biosensor for processing computation using a value of electric current flowing in the first electrode and the second electrode, thereby generating a calculated value; and an output unit operatively coupled to the signal processor for outputting the calculated value by the computation of the signal processor, whereby when the biosensor is provided with a sample solution containing a substrate, and is mounted in the sensor mounting portion, the amount of the substrate is calculated by the computation processing of the signal processor, and the calculated value is outputted to the outputting unit.

An advantage of the measuring apparatus having such structure is that the calculation of the amount of a targeted substrate in the biosensor as well as the output (display) of the calculated value can handily be performed.

The measuring apparatus can also be so structured that it further comprises a sensor ejection member provided at the sensor mounting portion for ejecting the biosensor to outside of the sensor mounting portion in a manner that the biosensor is provided with a push-out force by the ejection member.

Such measuring apparatus can further be so structured that the push-out force by the ejection member is provided to abutment between the ejection member and the second extension portion of the biosensor.

An advantage of such measuring apparatuses is that the biosensor mounted in the sensor mounting portion thereof can handily be ejected to outside of the sensor mounting portion or the measuring apparatus.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Hereinafter, embodiment modes (examples) of the present invention will be described with reference to the appended drawings. It is to be noted that these embodiment modes and the drawings are intended for illustrating examples of the present invention, and the present invention is not limited thereto.

Embodiment Mode 1

Figure 1A:
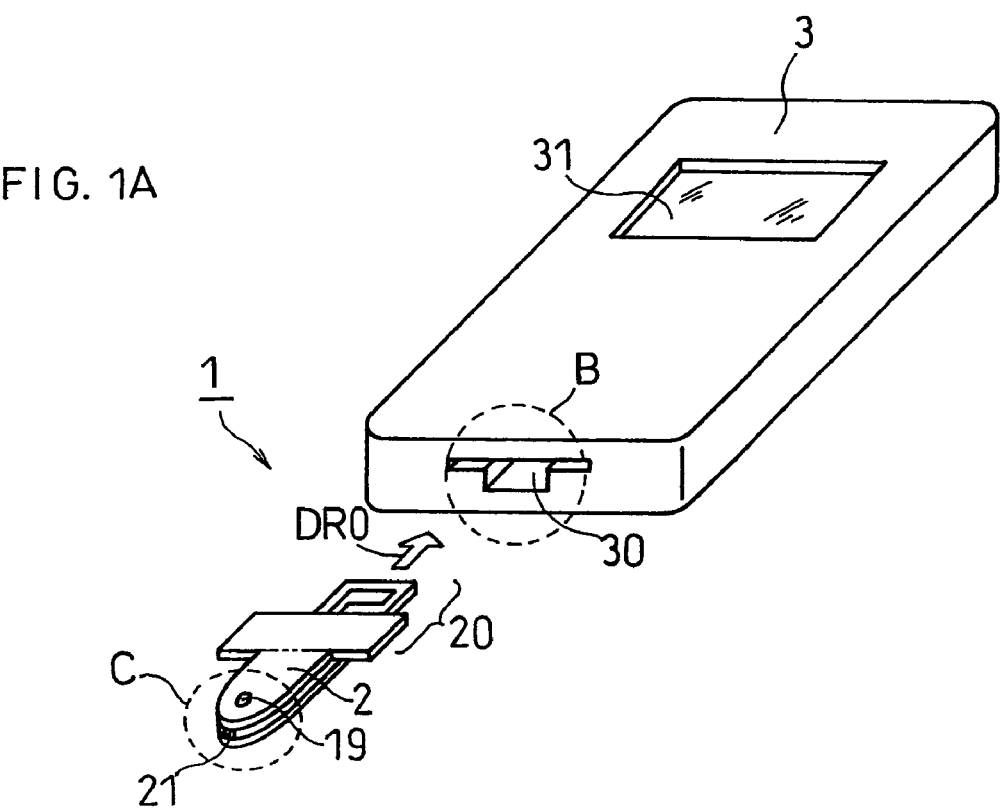
FIG. 1A is a schematic oblique view of a biosensor system according to EMBODIMENT MODE 1 of the present invention.
Figure 1B:
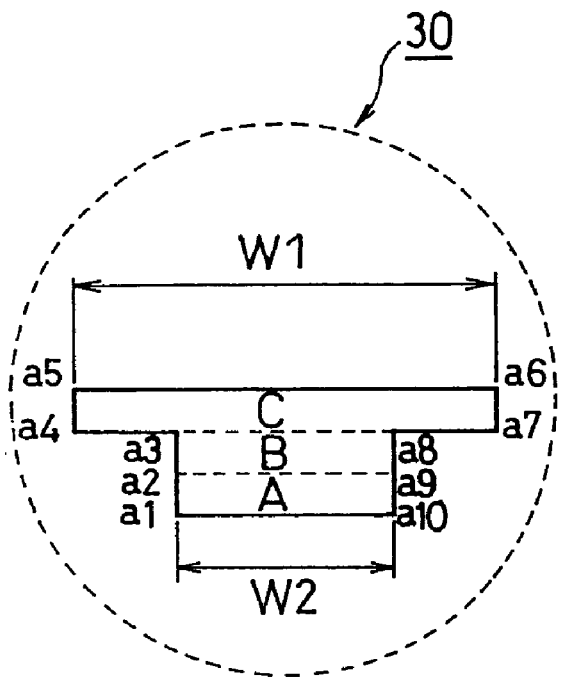
FIG. 1B is a schematic view, partially enlarged, of a part in FIG. 1A as encircled by dashed line circle B, which is sensor mounting portion 30 of measuring apparatus 3 as seen in the arrow direction DR0.
Figure 1C:
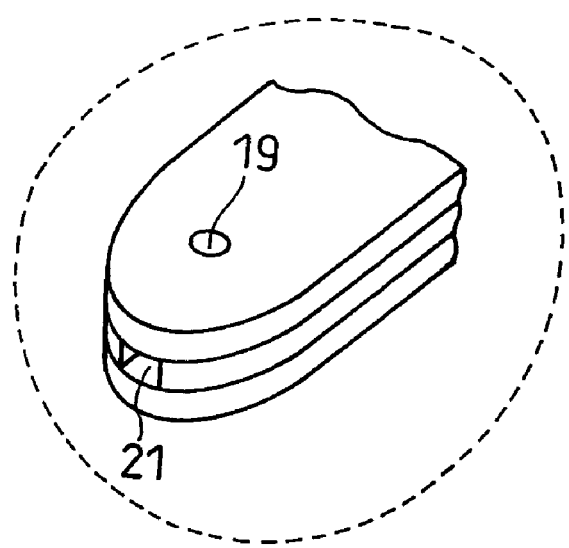
FIG. 1C is a schematic oblique view, partially enlarged, of a part of FIG. 1A as encircled by dashed line circle C, which is an end portion of biosensor 2.

FIG. 1A is a schematic oblique view of a biosensor system 1 according to EMBODIMENT MODE 1 of the present invention, and FIG. 1B is a schematic view, partially enlarged, of a part in FIG. 1A as encircled by dashed line circle B, which is a sensor mounting portion 30 of a measuring apparatus 3 as seen in the arrow direction DR0. Further, FIG. 1C is a schematic oblique view, partially enlarged, of a part of FIG. 1A as encircled by dashed line circle C, which is an end portion of the biosensor 2. The biosensor system 1 comprises the biosensor 2 and the measuring apparatus 3 for measuring biosensors, particularly for having the biosensor 2 mounted therein.

Before describing details of respective elements of the biosensor system 1, the measuring operation using the biosensor system 1 is briefly described as follows. In the present specification, the term measuring operations is used to mean the operation of quantifying a substrate in a sample solution as well as the operation of detecting existence of a substrate in the sample solution.

Referring to the above-described drawings, a mounting end portion 20 of the biosensor 2, which is an end portion of the biosensor 2 from the portion partitioned by the dashed double-dotted line shown in FIG. 1A to the edge thereof facing the measuring apparatus 3, is inserted by a user (not shown) into the sensor mounting portion 30 in the direction shown by an arrow DR0. The mounting end portion 20 has a shape at topside thereof different from a shape at downside thereof, and thus varies in a direction vertical to each main surface of the biosensor 2, which in turn is a stacking direction for stacking a pair of base plates of the biosensor as will be described later. The term "vertical direction" or "top-down direction" in the present specification is used to mean such stacking direction.

More specifically describing the difference of shape, an extension portion at the downside of the biosensor is extended in a direction different from that in which an extension portion at the topside of the biosensor is extended, as shown in FIG. 1A and as will be described later.

The sensor mounting portion constituted by space is formed for matching up with or corresponding to the shape of the mounting end portion 20, which has such different shapes at the topside and the downside as described above. Such shapes of the mounting end portion 20 and the sensor mounting portion 30 are greatly different from those in the case of conventional biosensors and measuring apparatuses. Owing to the unique shapes, the biosensor 2 can be mounted or inserted in the measuring apparatus 3 only when the posture of the sensor 2 is maintained for such mounting or insertion, such that the top-down direction or the topside and the downside of the biosensor match up with or correspond to the shape of the sensor mounting portion 30.

Next, a drop of sample solution is deposited by the user on a sample solution drop deposition portion 21 formed at an edge of the biosensor 2, which also has an air vent 19. For more clearly showing the structure of the drop deposition portion 21, the end portion of the biosensor encircled by the dashed line circle C is enlarged as shown in the partially enlarged view of FIG. 1C. The thus deposited drop of the sample solution is sucked into the inside of the biosensor 2 by capillary action. Then, a reagent (described later), which reacts with a substrate contained in the sample solution, is dissolved in the sample solution. Subsequently, a voltage is applied to the electrodes of the biosensor 2 using the measuring apparatus 3 (described later), and electrochemical change between the electrodes caused by the reaction of the reagent is detected thereby. The results of the measurement are displayed at a display unit (output unit) 31 of the measuring apparatus 3, thereby concluding the measuring operation.

Examples of sample solutions and substrates, which can be subjected to the measuring operation in the biosensor system 1 according to the present EMBODIMENT MODE 1, are as follows. Examples of sample solutions are biological fluids such as blood (either whole blood or non-cell components such as blood plasma and blood serum), interstitial fluid, skin fluid, sweat, tear and urine. Examples of substrates are glucose, cholesterol and lactic acid. Among them, the biosensor system 1 is particularly suitable for quantifying glucose, lactic acid and cholesterol in blood of a human body.

Hereinbelow, various elements of the biosensor system 1 will be more specifically described, with glucose contained in the blood of a human body being taken as an example of the substrate.

Figure 2A:
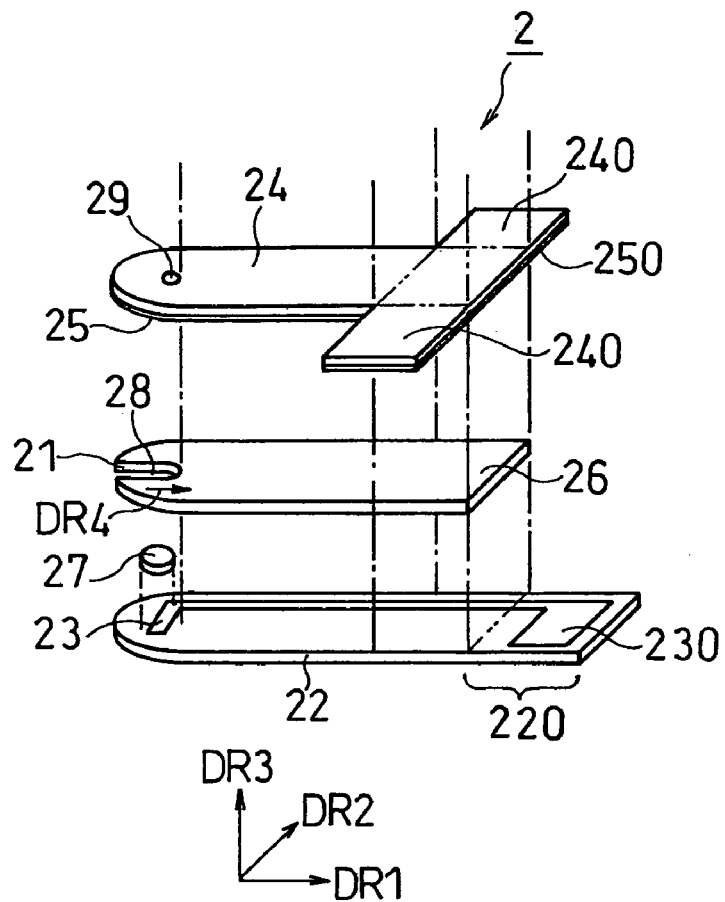
FIG. 2A is a schematic exploded oblique view of a biosensor according to EMBODIMENT MODE 1 of the present invention.
Figure 2B:
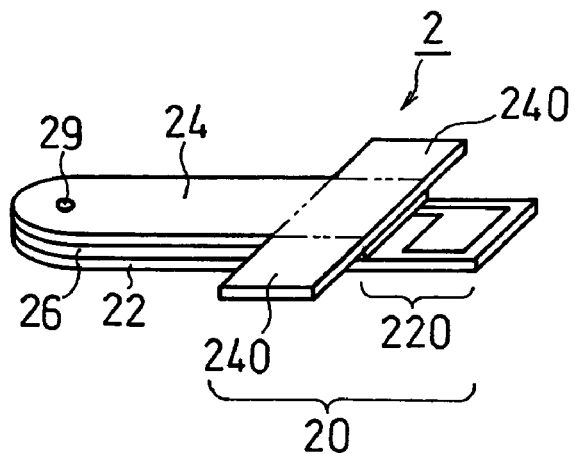
FIG. 2B is a schematic oblique view of the biosensor according to EMBODIMENT MODE 1 of the present invention.

First of all, respective constituting elements of biosensor 2 will be described with reference to FIG. 2A and FIG. 2B, in which FIG. 2A is a schematic exploded oblique view and FIG. 2B is a schematic oblique view of the biosensor 2.

A base plate (first base plate) supporting a working electrode 23 and a lead 230 electrically connected to the working electrode 23 is made of an electrically insulating material such as polyethylene terephthalate. This first base plate 22 has an extension portion 220 (first extension portion) thereof, relative to a later described second base plate 24, which extension extends in the length direction of the first base plate 22. The term "length direction" is used in the present specification to mean the direction parallel to the length of the base plate as indicated by arrow DR1 shown in FIG. 2A. With reference to FIG. 2A, the extension portion 220 is such portion of an end of the first base plate 22 from a partition line indicated by the dashed double-dotted line on the first base plate 22 to the edge of the first base plate. In other words, the first extension portion is a part of the first base plate 22, and extends in the length direction of the first base plate from a position corresponding to an end or edge in the length direction of the second base plate to a length edge thereof (to face later described measuring apparatus).

On the surface of the first base plate 22, an electrically conductive working electrode 23 (first electrode) and a lead 230 connected to (continued from) the working electrode are formed, e.g., by sputtering an electrically conductive material such as palladium on the surface of the first base plate, and then trimming using e.g. a laser beam. Herein, a part of the lead 230 is formed on the first extension portion 220 and exposed to outside.

On the other hand, a base plate (second base plate) supporting a counter electrode 25 and a lead 250 electrically connected to the counter electrode 25 is made of an electrically insulating material such as polyethylene terephthalate. This second base plate 24 has two extension portions 240 (each being second extension portion) thereof, relative to the first base plate 22, which extensions extend in the width direction of the second base plate 24. The term "width direction" is used in the present specification to mean the direction parallel to the width of the base plate as indicated by arrow DR2 shown in FIG. 2A. With reference to FIG. 2A, the two extension portions 240 are such portions of an end of the second base plate 24 from respective partition lines indicated by the dashed double-dotted lines on the second base plate 24, parallel to the length direction (DR1), to the width edges or wing edges of the second base plate.

In other words, each second extension portion is a part of the second base plate 24, and extends in the width direction of the second base plate from a position corresponding to an end or edge in the width direction of the first base plate to a width edge or wing edge thereof. These two second extensions may be more readily understood from later shown FIG. 3C, where one second extension is defined by four corner points p1, p5, p8 and p4, while the other second extension is defined by four corner points p6, p2, p3 and p7.

On the surface of the downside or back side of the second base plate 24, an electrically conductive counter electrode 24 (second electrode) and a lead 250 connected to (continued from) the counter electrode are formed, e.g., by sputtering an electrically conductive material such as palladium on the entire downside surface of the second base plate. Herein, the entire downside surfaces of the second extensions portions 240 are covered by a part of the lead 250. However, it is also possible to first sputter the electrically conductive material on the entire downside surface of the second base plate 24, and then to trim, e.g. using a laser beam, thereby forming the counter electrode 25 and the lead 250 on a part of the downside surface of the second base plate 24.

For keeping a distance between the working electrode 23 and the counter electrode 25, a spacer member 26 is used, which is made of an insulating material such as polyethylene terephthalate. This spacer member 26 has, at a central position of the front edge thereof, a notch portion or cut-out portion, which constitutes a drop deposition part 21 (for receiving a sample solution drop) and a sample solution supply path 28 by being sandwiched between the first base plate 22 and the second base plate 24. Further, the second base plate 24 has an air vent 29 positioned at an end position of the sample solution supply path 28.

Although a plate form member is used here for the spacer member, an adhesive can be used instead thereof in a manner than the adhesive is coated on one surface of one of the base plates, and is sandwiched by the two base plates, thereby forming an adhesive layer to be a spacer member by hardening the adhesive layer.

A reagent layer 27 is formed by coating, on the working electrode 23, a reagent containing at least an enzyme. The reagent is preferred to contain an electron mediator and a hydrophilic polymer. In the case of the biosensor system 1 according to the present EMBODIMENT MODE 1, glucose in the blood of a human body is to be quantified. Accordingly, glucose oxidase is used as an enzyme to be carried by the reagent layer 27, and potassium ferricyanide is used as the electron mediator, while carboxymethyl cellulose is used as the hydrophilic polymer.

Examples of materials usable for the first base plate 1, the second base plate 2 and the spacer member 26 are various thermoplastic resins such as polyethylene, polystyrene, polyvinyl chloride, polyamide and saturated polyester resins (including the above-exemplified polyethylene terephthalate) as well as thermosetting resins such as urea resin, melamine resin, phenol resin, epoxy resin and unsaturated polyester resins.

Examples of materials usable for the working electrode 23, the counter electrode 25 and the leads 230 and 250 are generally used electrically conductive materials such as gold, silver, platinum and carbon as well as the above-exemplified palladium. Here it is to be noted that the material to be used for the working electrode 23 can be the same as or different from the material to be used for the lead 230 connected to or continued from the working electrode 23. Similarly, the material for the counter electrode 25 can be the same as or different from the material for the lead 250. For example, the working electrode 23 and the counter electrode 25 can be made of carbon, while the leads 230 and 250 can be made of silver, which has a lower resistivity than that of carbon.

In the above exemplification, carboxymethyl cellulose is used for the hydrophilic polymer, but generally other materials can be used instead as well. Other examples usable as the hydrophilic polymer are hydroxyethyl cellulose, hydroxypropyl cellulose, methyl cellulose, ethyl cellulose, ethylhydroxyethyl cellulose, polyvinyl pyrrolidone, polyvinyl alcohol, polyamino acids (such as polylysine), polystyrene sulfonic acid, gelatin (and its derivatives), polyacrylic acid (and its salts), polymethacrylic acid (and its salts), starch (and its derivatives) and polymer of maleic anhydride (and polymers of its salts). Among them, more preferable hydrophilic polymers are carboxymethyl cellulose, hydroxyethyl cellulose and hydroxypropyl cellulose.

In the present EMBODIMENT MODE 1, glucose is used as the substrate, namely a target for measurement. However, generally, other substrates such as lactic acid and cholesterol can also be quantitatively measured by selecting a suitable enzyme and a suitable electron mediator, depending on or corresponding to a targeted substrate contained in a sample solution.

Examples of usable enzymes for respective substrates are as follows. For example, not only glucose oxidase, but also glucose dehydrogenase can be used for glucose. An example of enzyme for fructose is fructose dehydrogenase. An example of enzyme for lactic acid is lactic acid oxidase. Examples of enzymes for cholesterol are cholesterol oxidase and cholesterol esterase. An example of enzyme for xanthin is xanthin oxidase. Further, an example of enzyme for amino acid is amino acid oxidase.

Examples of electron mediators other than the above-exemplified potassium ferricyanide are p-benzoquinone, phenazine methosulfate, methylene blue and ferrocene derivatives as well as a combination of two or more of these materials.

These respective elements of the biosensor are stacked and assembled in the vertical direction as shown by five dashed dotted lines in FIG. 2A, vertically extending, showing position correspondences for the stacking. Thereby, the first base plate 22 and the second base plate 24 are so stacked to each other that the working electrode 23 and the counter electrode 25 are opposed to or face each other. Here, it is to be noted again that the stacking direction, e.g., of the working electrode 23 and the counter electrode 25 is referred to as top-down direction or vertical direction of the biosensor 2 (namely, direction as indicated by arrow DR3 in FIG. 2A).

The spacer member 26 is integrally sandwiched between the first base plate and the second base plate 24. The space of the notch portion between the two base plates is formed as the sample solution supply path 28. Further, the working electrode 23 is so defined by the notch portion of the spacer member 26 as to have a given area. Similarly, the area of the counter electrode 25 is also defined, by the notch portion of the spacer member 26, to be a given area. The working electrode 23 and the counter electrode 25 are arranged to be opposed to each other with the sample solution supply path 28 therebetween.

The drop deposition portion 21 for having a drop of the sample solution deposited thereon is an inlet of the sample solution supply path 28. A sample solution drop deposited on the drop deposition portion 21 is sucked by capillary action toward the air vent 29 in a substantially horizontal direction (arrow DR4 direction as shown in FIG. 2A). The reagent layer 27 is placed in the sample solution supply path 28 between the working electrode 23 and the counter electrode 25. FIG. 2B shows an oblique view of the biosensor 2 having been stacked and assembled with the position correspondences of the respective stacked elements as shown by the group of vertical dashed dotted lines (vertical to the respective base plates) in FIG. 2A. It is to be noted here that in FIG. 2B, illustration of some elements such as the counter electrode 25 and the lead 250 is omitted for convenience sake. Such kind of omission of illustrations is also made in later shown drawings such as FIG. 3B, FIG. 6B, FIG. 7B and FIG. 12.

The biosensor 2 thus has a shape formed by the stacked first base plate 22 and second base plate 24, which are different in shape from each other, whereby it is easy for a biosensor user to visually and tactilely recognize or discriminate the posture of the biosensor 2 between the topside and downside in the top-down or vertical direction, and between the front end and the rear end in the length direction. More specifically, the biosensor 2 has the first extension portion 220 and the second extension portions 240, which cause the biosensor to be unsymmetrical between the topside and the downside in the vertical direction, and also unsymmetrical between both ends in the length direction of the biosensor. Describing in another way, the topside of the biosensor has a shape different from that of the downside thereof, and the front end of the biosensor has a shape different from that of the rear end thereof. This feature will be described in more detail below with reference to FIG. 3A, FIG. 3B and FIG. 3C.

Figure 3A:
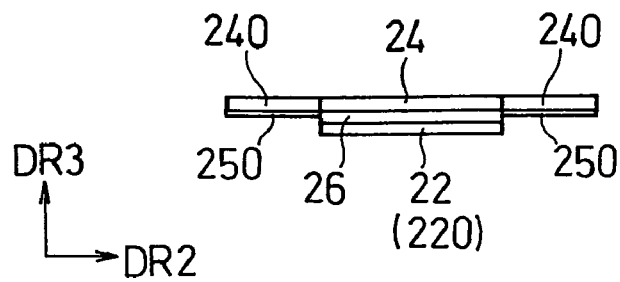
FIG. 3A is a schematic end view of the biosensor according to EMBODIMENT MODE 1 of the present invention.

FIG. 3A is a schematic end view of the biosensor 2 as seen from the end side, in the length direction, of the first extension portion 220 and the second extension portions 240 (namely, as seen from the direction opposite to the arrow DR1 direction as shown in FIG. 2A). The second base plate 24 has two second extension portions 240 extending relative to the first base plate 22 (having the first extension portion 220). In other words, the two second extension portions 240 extend, wing-wise and outwardly, from positions respectively corresponding to both ends of the first base plate 22 in its width direction in the horizontal plane.

Figure 3B:
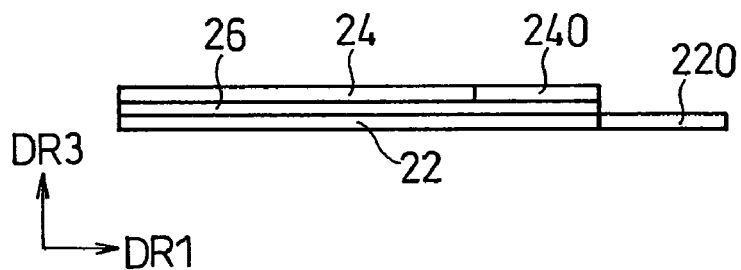
FIG. 3B is a schematic side view of the biosensor according to EMBODIMENT MODE 1 of the present invention.
Figure 3C:
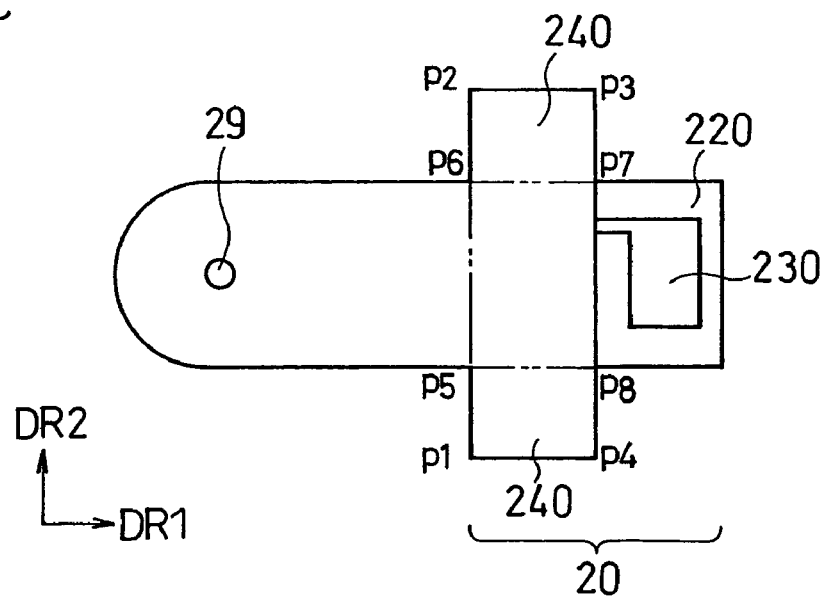
FIG. 3C is a schematic top plan view of the biosensor according to EMBODIMENT MODE 1 of the present invention.

Accordingly, as shown in the end view of FIG. 3A and the top plan view of FIG. 3C, the end face of the biosensor 2 is substantially T-shaped, and the top face of the biosensor 2 also is substantially T-shaped. Thereby, the topside and the downside in the vertical direction (namely, arrow DR3 direction in FIG. 2A and FIG. 3A) are unsymmetrical to each other, and the front end and the rear end in the length direction (namely, arrow DR1 direction in FIG. 2A and FIG. 3C) are also unsymmetrical to each other. Describing in another way, the topside of the biosensor has a shape different from that of the downside thereof, and the front end of the biosensor has a shape different from that of the rear end thereof. Thereby, it is easy for a biosensor user to correctly recognize the posture of the biosensor 2 in the top-down or vertical direction, and also in the length direction. More specifically, it is easy for a user to visually and tactilely discriminate the posture of the biosensor 2 between the topside and downside in the top-down or vertical direction (as to which one of the first base plate 22 and the second base plate 24 is positioned at the topside or downside), and between the front end and the rear end in the length direction (as to which one of the two ends is positioned at the front end or the rear end).

Further, as apparent from FIG. 3C, the second extension portions 240 as seen from above the topside thereof do not overlap the first base plate or the spacer member as to the occupying area on the sheet of FIG. 3, and extend wing-wise from the positions corresponding to both width ends of the first base plate. Describing in another way, the two second extension portions 240 are exposed to outside. Accordingly, the portions of the lead 250 formed on the downside surfaces of the second extension portions 240 are also exposed to outside. These exposed portions of the lead 250 are to be electrically connected to connectors (electric connection terminals) in the later described measuring apparatus 3, when the biosensor 2 is mounted in the measuring apparatus 3.

Since the lead 250 is thus partially exposed to outside, it becomes easy to electrically connect the lead 250 (and hence the counter electrode 25) to the connector in the measuring apparatus 3. In the case that the lead 250 is formed on the entire downside surface of the second base plate 24, the electric connection between the counter electrode 25 and the connector in the measuring apparatus 3 can be more secured, thereby avoiding poor electric connection therebetween. It is to be noted that this lead 250 and the counter electrode can be of two different layers, but also can of an integral layer. More specifically, the lead 250 and the counter electrode can be formed as a single layer, e.g., by forming the counter electrode and the lead 250 at the same time. In this latter case, the lead 250 can be considered as a part of the counter electrode having been formed to have an enlarged area to constitute the lead 250 as well.

FIG. 3B is a schematic side view of the biosensor 2 in the length direction (arrow DR1 direction in FIG. 2A and FIG. 3B), namely, the side view of the sensor as seen in the arrow direction DR2 in FIG. 2A. The first base plate 22 has the first extension portion 220 extending in the length direction relative to the second base plate 24 (having the second extensions 240). In other words, the first extension portion 220 extends outwardly in its length direction from a position corresponding to an edge of the second base plate in its length direction.

The biosensor 2 has an unsymmetrical shape due to the first extension portion 220, wherein with reference to FIG. 3B, the shape of the left portion shown in FIG. 3B is different from that of the right portion. Owing to this feature as well, a user can correctly recognize the length direction visually and tactilely. More specifically, when the biosensor 2 is mounted in the measuring apparatus 3, it is easy for the user to visually and tactilely discriminate as to whether the end of the biosensor at the first extension portion 220 faces the sensor mounting portion of the measuring apparatus, or the other end of the biosensor at the drop deposition portion 21 for the sample solution faces the sensor mounting portion.

Further, owing to the first extension portion 220, the biosensor has another unsymmetrical shape in the top-down direction (namely, the arrow DR3 direction in FIG. 2A and FIG. 3B), whereby the user can correctly recognize the posture of the biosensor 2 in such direction. More specifically, when the biosensor is mounted in the measuring apparatus 3, it is easy for the user to visually and tactilely discriminate as to which one of the first base plate 22 and the second base plate 24 is positioned at the topside or downside of the biosensor.

FIG. 3C is a schematic top plan view of the biosensor 2. As apparent from FIGS. 3B and 3C, the first extension portion 220 does not overlap the second base plate and the spacer member on the sheet of such drawings, and extends outwardly in the arrow DR1 direction. Thereby, a portion of the lead 230 formed on the first extension portion 220 is exposed to outside. This exposed portion of the lead 230 is to be connected to a later described connector in the measuring apparatus 3, when the biosensor 2 is mounted in the measuring apparatus 3.

Since the portion of the lead 230 is exposed to outside, it becomes easy to electrically connect the lead 230 to the connector in the measuring apparatus 3. The area of the lead 230 to be connected to the connector can be made large within the maximum possible area of the first extension portion 220. Thereby, the electric connection between the lead 230 and the connector in the measuring apparatus can be more secured, thereby avoiding poor electric connection.

It is to be noted that this lead 230 and the working electrode can be of two different layers, but also can of an integral layer. More specifically, the lead 230 and the working electrode can be formed as a single layer, e.g., by forming the working electrode and the lead 230 at the same time. In this latter case, the lead 230 can be considered as a part of the working electrode having been formed to have an enlarged area to constitute the lead 230 as well.

As evident from the foregoing descriptions, supposing the first extension portion 220 is removed from the first base plate 22, and the second extension portions 240 are also removed from the second base plate 24, the remaining part of the first base plate is similar and has a similar shape to that of the remaining part of the second base plate. Thus, according to the present specification, such remaining part of each base plate is referred to as common part thereof, whereas the first extension portion and the second extension portions are each referred to as non-common part thereof.

It is to be noted here that the second base plate 24 described above is provided with two of the second extension portions 240 symmetrically extending, from both width ends of the second base plate, to the left side and right side (left position and right position) of the second base plate in the length direction of the second base plate, namely with respect to the centerline on the second base plate in its length direction. However, it is also possible that the second base plate 24 is provided with only one of such second extension portions.

Further, it is also possible to so change the shapes of the first and the second base plates that the shape of the first extension portion 220 is replaced by the second extension portions 240. In other words, it is possible that the first base plate 22 has one or two first extension portion(s) extending outwardly in the width direction thereof from position(s) corresponding to a width edge(s) of the second base plate, and that the second base plate 24 has a second extension portion extending outwardly in the length direction thereof from a position corresponding to a length edge of the first base plate. In such case, it is necessary to make the shape of the sensor mounting portion 30 of the measuring apparatus 3 correspond to the changed shape of the biosensor having such changed shapes of the two base plates.

Next, the measuring apparatus 3, in which the biosensor 2 having been described with reference to FIGS. 1A, 1B, 2A, 2B, 3A, 3B and 3C, will be described in detail below with reference to FIG. 1A, FIG. 1B and FIG. 11.

The space constituting the sensor mounting portion 30 is shown in FIG. 1B, which is an enlarged view thereof. When the inlet of the sensor mounting portion 30 is seen in the direction to the inlet, namely, the arrow DR0 direction in FIG. 1A, the inlet is substantially T-shaped. This is because the shape of the sensor mounting portion 30 is needed to match up with or corresponding to the shape of the mounting end portion 20 (namely, the edge shape of the mounting end portion 20 as seen in the above-described direction. Because of such shape matching or shape correspondence, the biosensor 2 cannot be mounted upside down in the sensor mounting portion.

More specifically, as shown in the enlarged view of FIG. 1B, the space constituting the sensor mounting portion 30 seen in the DR0 direction as shown in FIG. 1A comprises three space segments, namely, space A (first sensor mounting segmental portion), space B and space C (second sensor mounting segmental portion), where the inlet of the space A is a rectangle defined by points a1, a2, a9 and a10 (where the points a1 and a10 are corner points, while the points a2 and a9 are midpoints between the points a1 and a3, and between the points a10 and a8, respectively) as shown in FIG. 1B, the inlet of the space B is a rectangle defined by points a2, a3, a8 and a9 as shown therein, and the inlet of the space C is also a rectangle defined by corner points a4, a5, a6 and a7 as shown therein. In other words, the space of the sensor mounting portion according to the present EMBODIMENT MODE has a slot shape formed by combining plural slots each having a shape of rectangular parallelepiped.

The space A corresponds to the first base plate 22 comprising the first extension portion 220 in the mounting end portion 20, and has a size suitable for having such end portion of the first base plate 22 fitted thereto. The space B corresponds to the spacer member 26 in the mounting end portion 20, and has a size suitable for having such end portion of the spacer member 26 fitted thereto. Further, the space C corresponds to the second base plate 24 comprising the second extension portions 240 in the mounting end portion 20, and has a size suitable for having such end portion of the second base plate 24 fitted thereto.

It is to be noted that the term "suitable size" is used herein to mean width, thickness and depth of space to be fitted to respective elements of the biosensor 2, where the width, the thickness and the depth of the space of the sensor mounting portion 30 refer to the dimensions thereof defined in the directions matching up with or corresponding to the width direction, the top-down (vertical) direction and the length direction of the biosensor 2, respectively, when the biosensor 2 is mounted in the sensor mounting portion.

The space A for having the first base plate 22 fitted thereto has width W2 which is smaller than width W1 of the space C for having fitted thereto the second base plate 24 comprising the second extension portions 240. Accordingly, the space A cannot have fitted thereto the second base plate 24, which is wider than the space A. For this reason, the biosensor 2 cannot be mounted by the user in the sensor mounting portion upside down, namely, in a top-down inverse direction (with the second base plate 24 being downside, and the first base plate 22 being topside) in contrast to the normal top-down direction (with the second base plate 24 being topside, and the first base plate 22 being downside).

Further, the space C for having the second base plate 24 fitted thereto has a depth smaller than that of the space A for having fitted thereto the first base plate 22 comprising the first extension portion 220. For this reason, the biosensor 2 cannot be mounted by the user in the sensor mounting portion front end back, namely, in a reverse length direction (with the drop deposition portion 21 being front side toward the sensor mounting portion 30, and the mounting end portion 20 being rear side or backside) in contrast to the normal length direction (with the drop deposition portion 21 being rear side or backside, and the mounting end portion 20 being front side to toward the sensor mounting portion 30).

Using the manner and the structure as described above, wrong insertion (in top-down inverse direction or reverse length direction) of the biosensor 2 into the measuring apparatus 3 can be securely prevented.

The structure of the sensor mounting portion 30 as described above will be further described in detail below with reference to FIG. 11, which is a schematic perspective view, showing the sensor mounting portion 30 provided at an end portion of a housing of the measuring apparatus 3. The points a1 to a10 as shown in FIG. 1B are also shown on an end face of the housing in FIG. 11. On the other hand, corner points b1 to b10 are those respectively positioned at positions corresponding to the points a1 to a10 and being extended and distanced from these points a1 to a10 in the direction of inserting the biosensor 2 (namely the arrow DR0 direction) by a distance substantially corresponding to the length of each second extension portion 240 (length in the arrow DR0 direction).

Meanwhile, corner points c1, c2, c9 and c10 are those respectively positioned at positions corresponding to the corner points b1, b2, b9 and b10 and being extended and distanced from these corner points b1, b2, b9 and b10 in the direction of inserting the biosensor 2 (namely the arrow DR0 direction) by a distance substantially corresponding to the length of the first extension portion 220 (length in the arrow DR0 direction).

Figure 11:
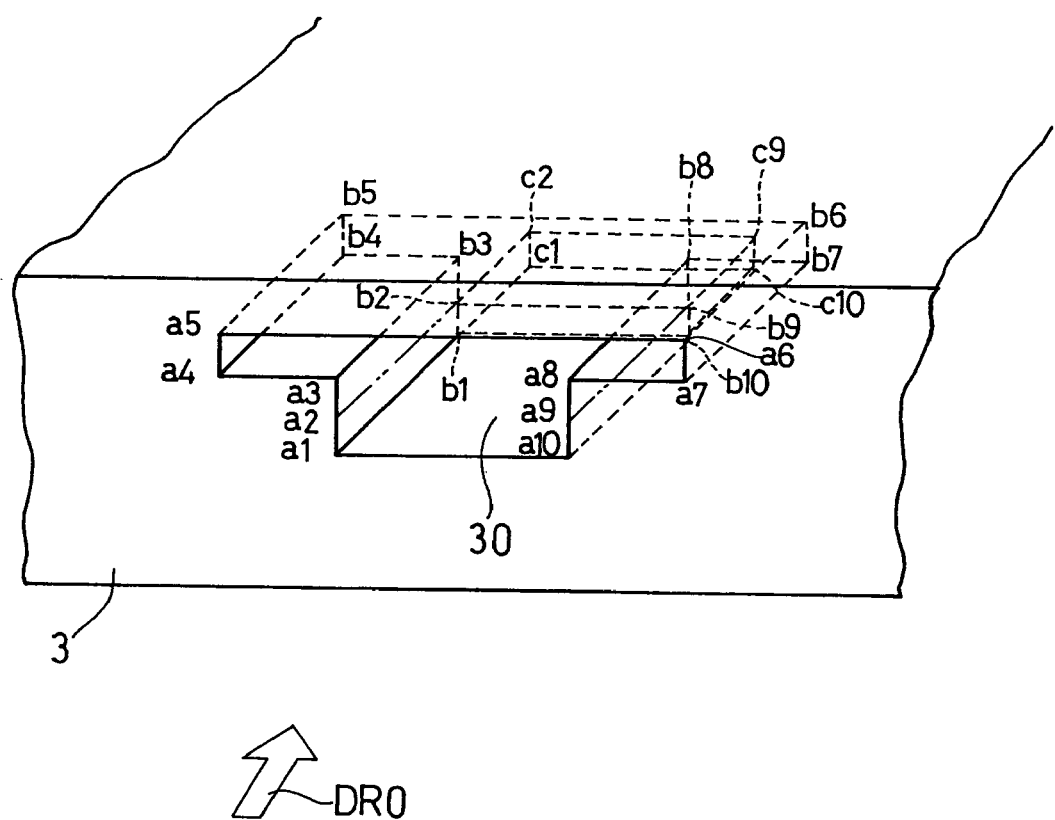
FIG. 11 is a schematic perspective view of a sensor mounting portion of the measuring apparatus.

Thus, the sensor mounting portion 30 has such structure, for example, that the end portion of the second base plate 24 (namely, the portion defined by the corner points p1, p2, p3 and p4 in FIG. 3C), which is composed of the two second extension portions 240 and the end portion of the second base plate positioned between the two second extension portions 240 (namely, the portion defined by the corner points p5, p6, p7 and p8 in FIG. 3C) as shown in FIG. 2B, is fitted to or corresponds to a rectangular parallelepiped space (namely, second sensor mounting segmental portion) defined by the corner points a4, a5, a6, a7, b4, b5, b6 and b7 as shown in FIG. 11.

Similarly, it is so structured that the end portion of the spacer member 26 is fitted to or corresponds to a rectangular parallelepiped space defined by the points a2, a3, a8, a9, b2, b3, b8 and b9. Also, it is so structured that the first extension portion 220 is fitted to or corresponds to a rectangular parallelepiped space (namely, a part of first sensor mounting segmental portion) defined by the corner points b1, b2, b9, b10, c1, c2, c9 and c10 as shown in FIG. 11.

Adding a description of electric connection with reference to FIG. 11, an electric connection terminal (connector) is provided on each of a face defined by the corner points a3, a4, b3 and b4 and a face defined by the corner points a7, a8, b7 and b8 so that the electric terminal contacts each portion of the leads (250) provided on the downside surfaces of the two second extension portions (240). Furthermore, an electric connection terminal (connector) is also provided on a face (downside face, facing the space corresponding to the first extension portion 220) defined by the corner points b2, b9, c2 and c9, so that such electric connection terminal contacts the lead (230) provided on the first extension portion (220).

Hereinafter, measuring operation of the biosensor system having the biosensor 2 mounted in the measuring apparatus 3 will be described with reference to FIG. 4 as well as FIGS. 1A, 1B, 2A, 2B, 3A, 3B and 3C.

Figure 4:
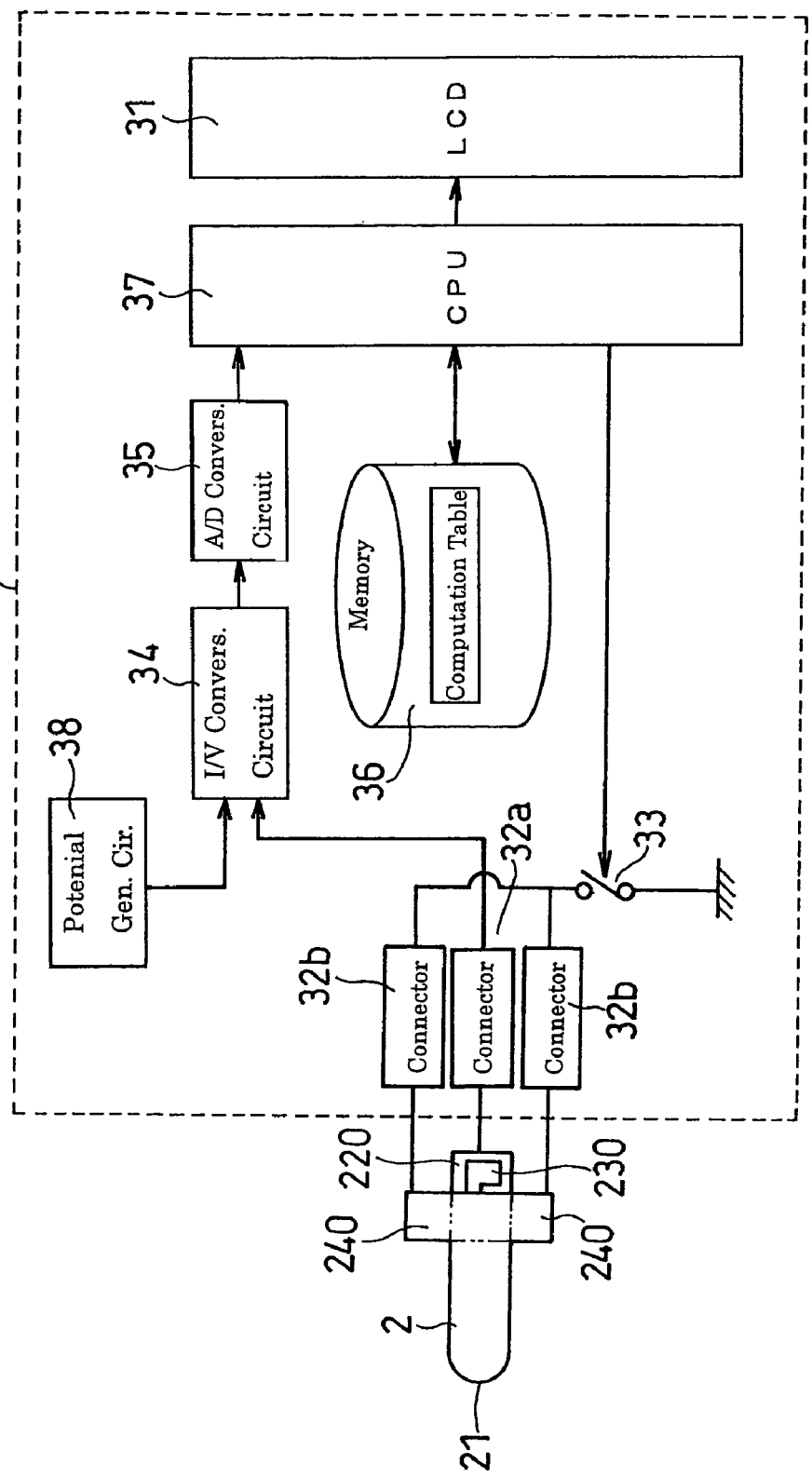
FIG. 4 is a schematic block diagram, showing an example of a connection of a biosensor to a measuring apparatus (biosensor system) according to EMBODIMENT MODE 1 of the present invention.

FIG. 4 is a schematic block diagram showing a biosensor 2 (top plan view) and a measuring apparatus 3. In the measuring apparatus 3, a connector (connection terminal) 32a is electrically connected to a lead 230 provided on the first extension portion 220 of the biosensor 2 and exposed to outside, while connectors (connection terminals) 32b are electrically connected to portions of lead (250 not shown in FIG. 4, but e.g. in FIG. 2A) provided on the second extension portions 240 and exposed to outside.

A switch 33 is provided between each connector 32b and ground (which means constant potential, and which is not necessarily zero). A potential generation circuit 38 is connected to a current-voltage (I/V) conversion circuit 34. The current-voltage conversion circuit 34 is electrically connected to the connector 32a. The value of the voltage outputted from this current-voltage conversion circuit 34 is converted to pulses by an A/D conversion circuit 35.

In the measuring apparatus, furthermore, a memory 36 is provided which has a computation table. The computation table is such table that has data showing relation between number of pulses outputted from the A/C conversion circuit 35 and glucose concentration in blood.

A central processing unit (CPU) 37 conducts various operations, including on-off switching of the switch 33, and measuring operation and computing operation on the basis of the number of pulses outputted from the A/D conversion circuit 35 and the computation table stored in the memory 36, thereby producing a calculated value corresponding to a targeted substrate (glucose) in the sample solution. The calculated value is displayed on a display unit of a liquid crystal display (LCD) 31. Instead of using such display unit, it is also possible to provide a voice synthesizer as an output unit for acoustically outputting the calculated value to outside. It is also possible to output the calculated value in other ways, such as using a hard disk in an external personal computer for storing the calculated value therein, namely outputting, through a network, to outside of the measuring apparatus.

Next, operation of substrate measurement, using the above-described system, will be described as follows. A user deposits a drop of blood (sample solution) on the sample solution drop deposition portion 21, after the biosensor 2 is mounted in the measuring apparatus 3. The thus deposited drop of blood is sucked into the sample solution supply path 28 by capillary action. Then, a reagent layer (not shown in FIG. 4, but shown e.g. in FIG. 2A by reference numeral 27) is dissolved in the blood, and oxidation-reduction reaction of an electron mediator in the reagent layer progresses.

More specifically, glucose oxidase, which is an enzyme carried by the reagent layer, and potassium ferricyanide, which is an electron mediator, are dissolved in the blood. Thereby, enzyme reaction between the glucose in the blood and the glucose oxidase progresses, thereby generating electrons. The potassium ferricyanide is thus reduced to potassium ferrocyanide by such generated electrons.

Further, owing to the existence of carboxymethyl cellulose in the reagent layer, adsorption of certain materials in the blood such as protein to the surface of the working electrode is suppressed, whereby the electrode reaction well progresses. Thereby, furthermore, the influence of e.g. physical shocks imposed on the biosensor, which is attributed to an increase of viscosity of the sample solution during the measurement, is mitigated, thereby decreasing variations of sensor responses.

The CPU 37 is so designed as to turn the switch 33 on at a certain time point after the start of the measurement. Thereby, a certain potential difference (potential difference between the potential of the ground and the potential generated by the potential generation circuit 38) is generated between the working electrode 23 and the counter electrode 25 via the connectors 32a and 32b and respective leads connected to the electrodes. In other words, a certain voltage, with the potential of the counter electrode 25 being as a reference, is applied to the working electrode 23.

Then, the potassium ferrocyanide, which is a reduction product of potassium ferricyanide, is oxidized back to potassium ferricyanide, whereby an electric current flows between the working electrode 23 and the counter electrode 25 in proportion to the concentration of glucose in the blood.

According to the present biosensor 2 as described in the present EMBODIMENT MODE 1, the working electrode 23 and the counter electrode 25 are opposed to each other with the sample solution supply path 28 therebetween. Accordingly, ion transfer well progresses therebetween. Thus, even when the drop of the blood to be measured is of a trace amount, an electric current proportional to the glucose concentration flows. Accordingly, the measuring apparatus 3 can be used for conducting measuring operation with high sensitivity even for a trace amount of blood.

It is to be noted that in the present specification, the term "trace amount" of blood or sample solution is used to mean such amount that is smaller than that as required in the case of biosensors in which a working electrode and a counter electrode are arranged on a single plane in contrast to biosensors of the electrode-opposed type.

The electric current proportional to the glucose concentration is converted to a voltage by the current-voltage conversion circuit 34. Such voltage value is further converted to pulses by the A/D conversion circuit 35, and is then fed to the CPU 37. The CPU 37 counts the number of such pulses, and conducts computation based on the computation table stored in the memory 36, thereby calculating the glucose concentration in the blood. The calculated value is displayed on the LCD (display unit) 31, thereby concluding quantitative measurement or quantification of glucose in the blood.

Regarding the shapes of the first extension portion 220 and the second extension portions 240, the biosensor as described above has specific shapes as apparent from the foregoing. However, it is of course possible to modify the shapes within such concept of the present invention or the present EMBODIMENT MODE that the user and the measuring apparatus can recognize and discriminate required factors as described above. One example of such modification is shown in FIG. 12, which is a schematic oblique view of a biosensor 12 modified from that, e.g., of FIG. 2B.

Figure 12:
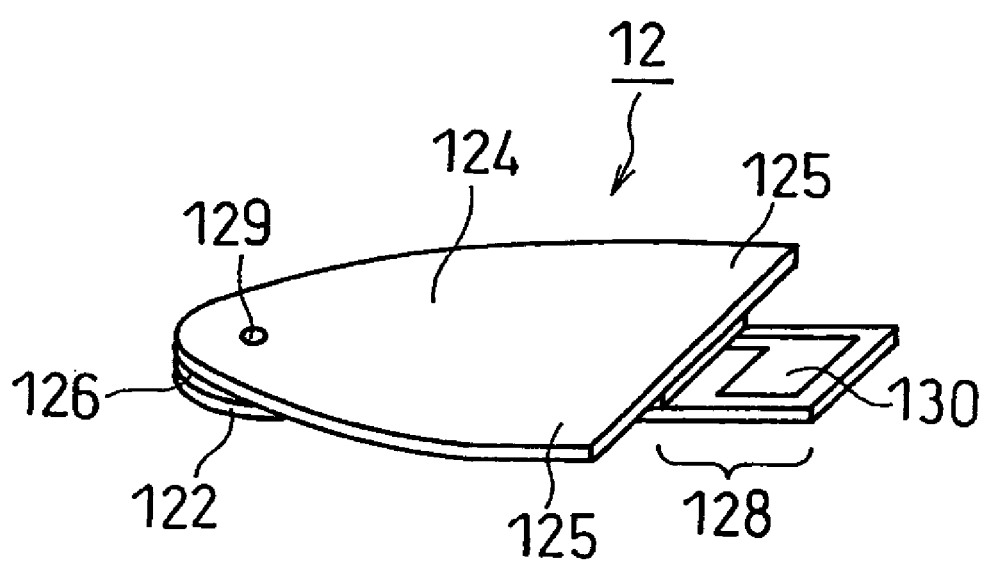
FIG. 12 is a schematic oblique view of a modified example of a biosensor of the present invention.

Referring to FIG. 12, a spacer member 126 is sandwiched between a first base plate and a second base plate 124. At an end of the first base plate, a first extension portion 128 is provided. On the first extension portion 128, a lead 130 is provided in a manner that a portion of the lead is exposed to outside. On the second base plate 124, an air vent 129 is provided.

A feature of this biosensor 12 is that each one of second extension portions 125 is so designed that its width gradually increases from its one end of the second base plate 124 at the side of the air vent 129 to the other end thereof where the first extension portion 130 is provided on the first base plate 122. This is in contrast to the biosensor 2 as shown, e.g., in FIG. 2B, in which each of the second extension portions 240 has a rectangular shape extending in the width direction of the second base plate from the position corresponding to each width edge of the first base plate as described above. Such structure of the biosensor as shown in FIG. 12 can also solve an underlying problem and achieve an object according to the present EMBODIMENT MODE or the present invention.

As in the case of the biosensors as described above, it is possible to so change the shapes of the first and the second base plates of the biosensor 12 that the shape of the first extension portion 128 is replaced by the second extension portions 125. In other words, it is possible that the first base plate 122 has one or two first extension portion(s) extending outwardly in the width direction thereof from position(s) corresponding to a width edge(s) of the second base plate 124, and that the second base plate 124 has a second extension portion extending outwardly in the length direction thereof from a position corresponding to a length edge of the first base plate. In such case, it is necessary to make the shape or space of the sensor mounting portion of the measuring apparatus correspond to the changed shape of the biosensor having such changed shapes of the two base plates, but it is easy to make such design change of the sensor mounting portion.

Embodiment Mode 2

This EMBODIMENT MODE 2 is different from EMBODIMENT MODE 1 in that, in this EMBODIMENT MODE 2, plural different biosensors having different measurement targets are subjected to measurements by one measuring apparatus. In the following, description will be made with respect mainly to such different points.

Figure 5A:
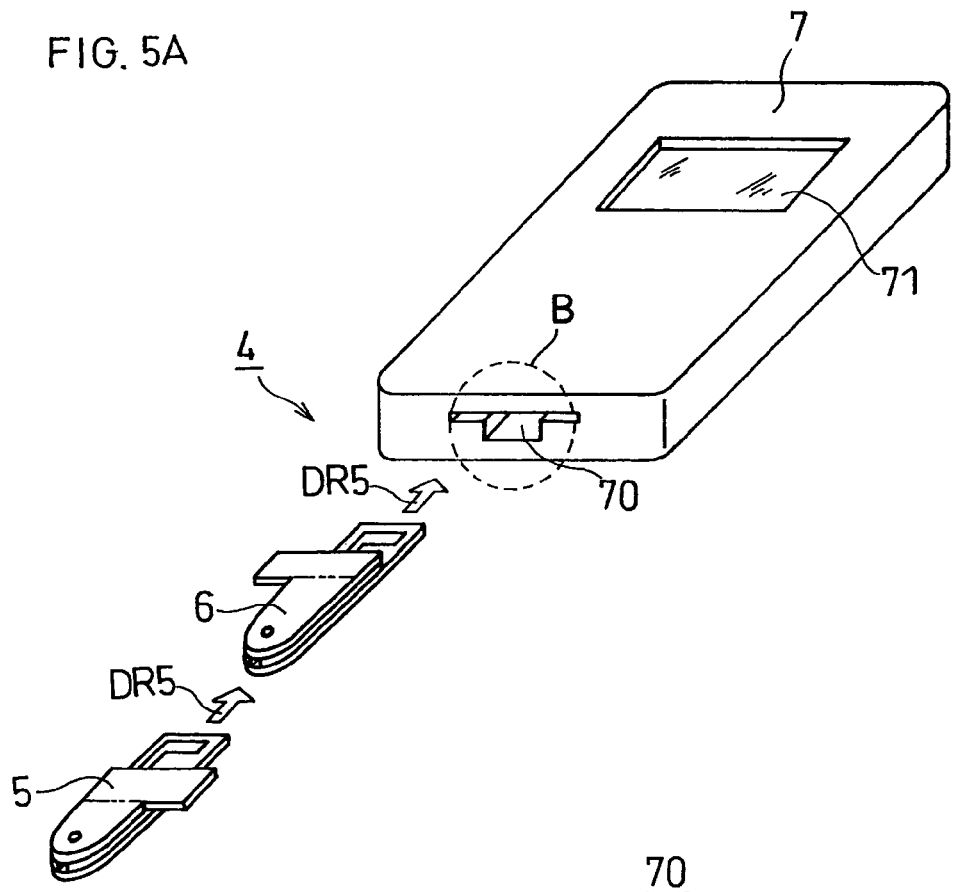
FIG. 5A is a schematic oblique view of a biosensor system according to EMBODIMENT MODE 2 of the present invention.
Figure 5B:
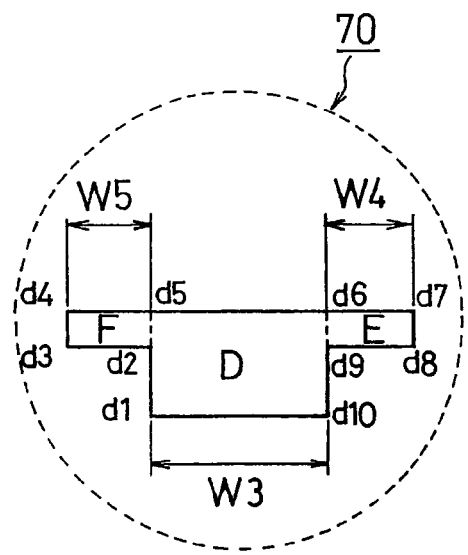
FIG. 5B is a schematic view, partially enlarged, of a part in FIG. 5A as encircled by dashed line circle B, which is sensor mounting portion 70 of measuring apparatus 7 as seen in the arrow direction DR5.

FIG. 5A is a schematic oblique view of a biosensor system 4 according to the present EMBODIMENT MODE 2, while FIG. 5B is a schematic enlarged view of a portion encircled by dashed line circle B in FIG. 5A (namely, end face of sensor mounting portion 70 of measuring apparatus 7 as seen in arrow DR5 direction). The biosensor system 4 comprises a biosensor 5, a biosensor 6 and a measuring apparatus 7 (measuring apparatus for biosensor) in which each such biosensor is mounted for measuring operation. This biosensor system 4 is briefly described below.

The biosensor 5 is different from the biosensor 6 with respect to the measurement targets. More specifically, the targeted substrate of the biosensor 5 is different from that of the biosensor 6. In other words, each one of the biosensors 5 and 6 corresponds to each specific substrate. For this reason, the shape of the biosensor 5 is different from that of the biosensor 6. In other words, each one of the biosensors 5 and 6 corresponds to each specific shape. A user thus can easily make visual and tactile discrimination between the two different biosensors owing to the difference in shape between the two biosensors.

The measuring apparatus 7 comprises a sensor mounting portion 70 for mounting both of the biosensors 5 and 6. The sensor mounting portion 70 has such shape that can mount each of such biosensors, only when each biosensor is mounted in a correct direction with the posture of the biosensor being correctly maintained for the mounting thereof, such that the top-down direction (vertical direction) as well as front-rear direction (length direction) of the biosensor match up with or correspond to the shape of the sensor mounting portion 70, thereby avoiding wrong insertion of each biosensor (in top-down inverse direction or reverse length direction).

The measuring apparatus 7 discriminates between the respectively different biosensors on the basis of the space, which is occupied by the mounted biosensor, or on the basis of the position where the mounted biosensor contacts the sensor mounting portion 70. The measuring apparatus 7 conducts measuring operation in accordance with the discriminated biosensor, and displays (outputs) the results of the measurements at the display unit (output unit) 71 made, e.g. of an LCD. Thereby, a user, using one measuring apparatus 7, can measure plural different biosensors having different measurement targets.

Just as in the case of the EMBODIMENT MODE 1, Examples of sample solutions and substrates, which can be subjected to the measuring operation in the biosensor system 4 according to the present EMBODIMENT MODE 2, are as follows. Examples of sample solutions are biological fluids such as blood, interstitial fluid, skin fluid, sweat, tear and urine. Examples of substrates are glucose, cholesterol and lactic acid. Among them, the biosensor system 4 is particularly suitable for quantifying glucose, lactic acid and cholesterol in blood of a human body. The difference of the EMBODIMENT MODE 2 from the EMBODIMENT MODE 1 is in that at least two substrates can be subjected to the measuring operation in the present EMBODIMENT MODE 2.

Hereinbelow, various elements of the biosensor system 4 will be more specifically described, with glucose and lactic acid contained in the blood of a human body being taken as examples of the substrates.

Figure 6A:
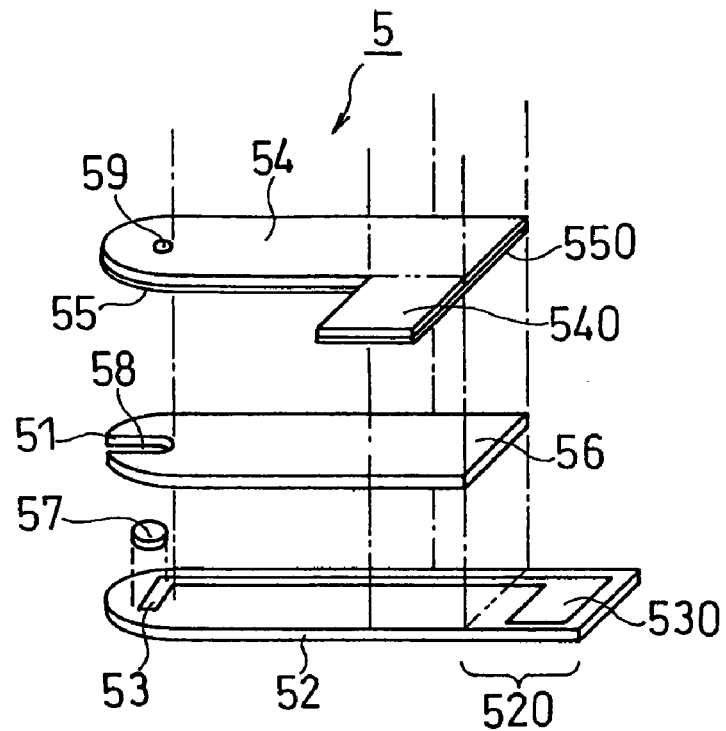
FIG. 6A is a schematic exploded oblique view of a biosensor according to EMBODIMENT MODE 2 of the present invention.
Figure 6B:
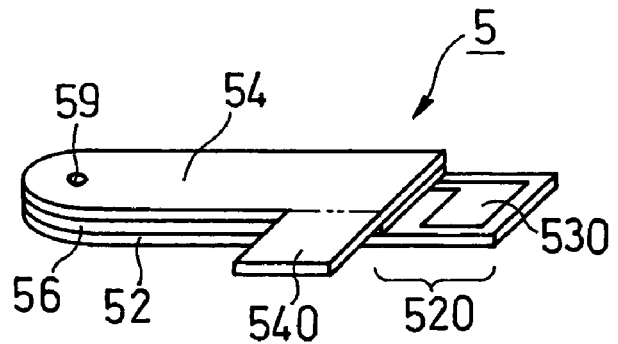
FIG. 6B is a schematic oblique view of the biosensor according to EMBODIMENT MODE 2 of the present invention.
Figure 7A:
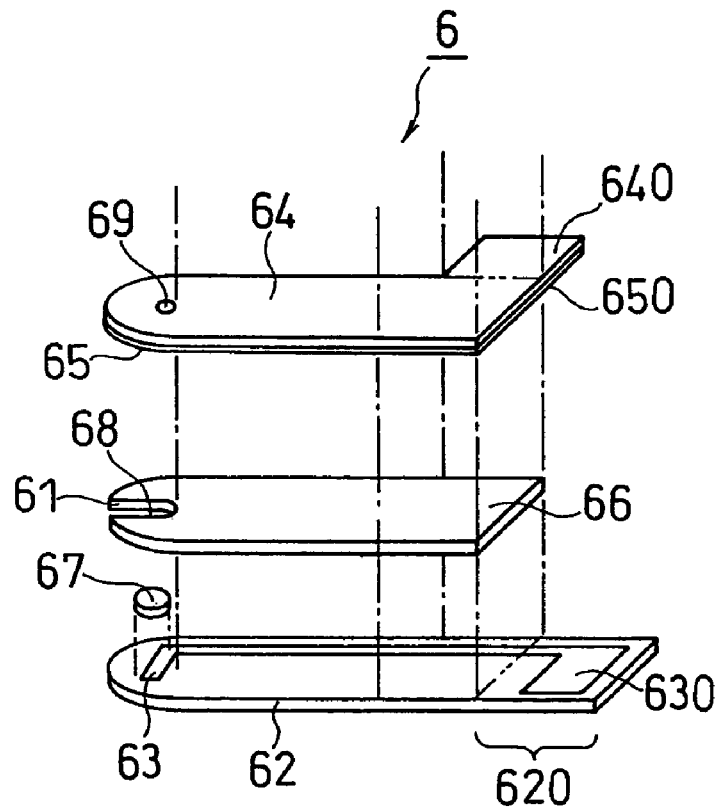
FIG. 7A is a schematic exploded oblique view of a further biosensor according to EMBODIMENT MODE 2 of the present invention.
Figure 7B:
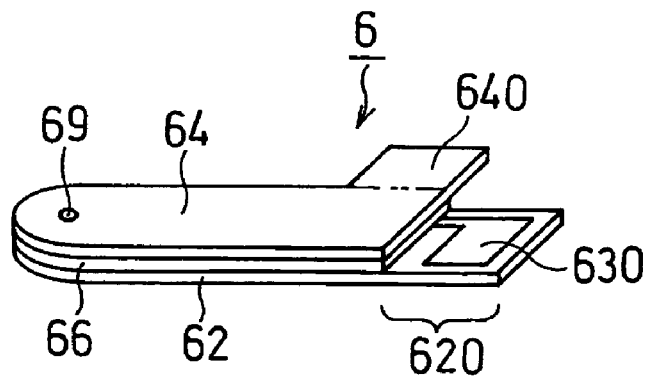
FIG. 7B is a schematic oblique view of the further biosensor according to EMBODIMENT MODE 2 of the present invention.

First, the biosensors 5 and 6 will be described with reference to FIGS. 6A and 6B and FIGS. 7A and 7B, respectively. Among them, FIG. 6A is a schematic exploded oblique view of the biosensor 5, while FIG. 6B is a schematic oblique view of the biosensor 5. Further, FIG. 7A is a schematic exploded oblique view of the biosensor 6, while FIG. 7B is a schematic oblique view of the biosensor 6.

The biosensor 5 is a biosensor (glucose sensor) for measuring glucose contained in blood. The biosensor 5, as shown in FIG. 6A, comprises a drop deposition portion 51 (for sample solution drop), a first base plate 52 (for working electrode), a first extension portion 520 (end portion of the first base plate 52 extending outwardly from the position indicated by dashed double-dotted line provided on the first base plate 52 in its length direction as shown in FIG. 6A), a working electrode (first electrode) 53, a lead 530 (continued from the first electrode 53 and provided on the first base plate 52 to extend to the topside surface of the first extension portion 520), a second base plate 54 (for counter electrode), a second extension portion 540 (portion of the second base plate 54 extending outwardly from the position indicated by dashed double-dotted line provided on the second base plate 54 in its width direction as shown in FIGS. 6A and 6B), a counter electrode (second electrode) 55, a lead 550 (continued from the second electrode and provided on the second base plate to extend to the downside surface of the second extension portion 540), a spacer member 56, a reagent layer 57, a sample solution supply path 58 and an air vent 59.

These respective elements have structures and functions similar to those of the biosensor 2 in the EMBODIMENT MODE 1, which are referred to by mutually the same names (except for the second extension portion), so that detailed description thereof is omitted here. Just as in the case of the EMBODIMENT MODE 1, the terms such as top-down (vertical) direction, length direction and width direction are used here for the same meanings. For example the top-down direction is the direction of stacking the respective base plates.

The difference between the biosensor 5 and the biosensor 2 is in the shape of the second base plate, more specifically in the shape of the second extension portion 540. That is, the second extension portion 540 of the biosensor 5 extends in the width direction from only one side of the second base plate relative to the first base plate 52. More specifically, the second extension portion 540 extends outwardly from a position corresponding to only one of width edges of the first base plate 52. The side of second extension portion 540 is right side, as seen to the arrow DR5 direction shown in FIG. 5A in mounting the biosensor 5 in the measuring apparatus 7, with the second base plate 54 being maintained on the topside, and the first base plate 52 being maintained on the downside of the biosensor 5.

These respective elements of the biosensor as shown in FIG. 6A are stacked and assembled in the vertical direction as shown by five dashed dotted lines in FIG. 6A, vertically extending, showing position correspondences for the stacking. Thereby, the biosensor 5 as shown in FIG. 6B is formed. The arrangements of the respective elements in the schematic oblique view in FIG. 6B have similar structures and functions to those of the biosensor 2 (except for the second extension portion), which are referred to by mutually the same names, so that detailed description thereof is omitted here.

The thus structured biosensor 5 has an advantage in that because of the stacking of the mutually different base plates (first base plate 52 and second base plate 54), it is easy for a user to visually and tactilely recognize and discriminate between the topside and the downside (in the vertical direction), and between the front side and rear side (in the length direction) of the biosensor 5.

The biosensor 6 is a biosensor (lactic acid sensor) for measuring lactic acid contained in blood. The biosensor 6, as shown in FIG. 7A, comprises a drop deposition portion 61 (for sample solution drop), a first base plate 62 (for working electrode) and a first extension portion 620 (end portion of the first base plate 62 extending outwardly from the position indicated by dashed double-dotted line provided on the first base plate 62 in its length direction as shown in FIG. 7A).

Here, it is preferred that the first extension portion 620 have the same shape and size as those of the first extension portion 520 in order to simplify the structure of the measuring apparatus 7.

The biosensor 6 further comprises a working electrode (first electrode) 63, a lead 630 (continued from the first electrode 63 and provided on the first base plate 62 to extend to the topside surface of the first extension portion 620), a second base plate 64 (for counter electrode), a second extension portion 640 (portion of the second base plate 64 extending outwardly from the position indicated by dashed double-dotted line provided on the second base plate 64 in its width direction as shown in FIGS. 7A and 7B), a counter electrode (second electrode) 65, a lead 650 (continued from the second electrode and provided on the second base plate to extend to the downside surface of the second extension portion 640), a spacer member 66, a reagent layer 67, a sample solution supply path 68 and an air vent 69.

These respective elements have structures and functions similar to those of the biosensor 5 above, which are referred to by mutually the same names (except for the second extension portion), so that detailed description thereof is omitted here.

As evident from the above descriptions, the biosensor 6 is different from the biosensor 5 with respect to the following two points.

A first point is in the extending direction of the second extension portion provided on the second base plate. More specifically, the width direction in which the second extension portion 640 in FIG. 7A or 7B extends is opposite to the width direction in which the second extension portion 540 in FIG. 6A or 6B extends, whereby the shape of the second base plate in FIG. 7A or 7B is different from that of the second base plate in FIG. 6A or 6B.

Thus, the side of second extension portion 640 is left side, as seen to the arrow DR5 direction shown in FIG. 5A in mounting the biosensor 6 in the measuring apparatus 7, with the second base plate 64 being maintained on the topside, and the first base plate 62 being maintained on the downside of the biosensor 6. Accordingly, it can be said that the non-common part of the second base plate of each of the biosensors 5 and 6 has a specific shape. More specifically, the position of the second extension portion of each biosensor, which is the non-common part of the second base plate, is a specific position for each biosensor.

A second point is in the reagent in the reagent layer. The reagent layer 67 comprises an electron mediator and a hydrophilic polymer similar to those in the reagent layer 57. However, in the reagent layer 67, a lactic acid oxidase is used as an enzyme in place of glucose oxidase used as an enzyme in the reagent layer 57.

Summarizing the first point and the second point as described above, the non-common part of the second base plate has a specific shape or positioned at a specific position, corresponding to a specific substrate in the reagent layer, in both cases of the biosensors 5 and 6.

These respective elements of the biosensor as shown in FIG. 7A are stacked and assembled in the vertical direction as shown by five dashed dotted lines in FIG. 7A, vertically extending, showing position correspondences for the stacking. Thereby, the biosensor 6 as shown in FIG. 7B is formed. The arrangements of the respective elements in the schematic oblique view in FIG. 7B have similar structures and functions to those of the biosensor 5 (except for the second extension portion), which are referred to by mutually the same names, so that detailed description thereof is omitted here.

The thus structured biosensor 6 has an advantage in that because of the stacking of the mutually different base plates (first base plate 62 and second base plate 64), it is easy for a user to visually and tactilely recognize and discriminate between the topside and the downside (in the vertical direction), and between the front side and rear side (in the length direction) of the biosensor 6.

Furthermore, the second base plate 64 of the biosensor 6 has a shape different from that of the second base plate 54 of the biosensor 5, because the second extension portion 640 of the biosensor 6 extends to a width direction opposite to the width direction to which the second extension portion 540 of the biosensor 5 extends. In other words, each of the second base plates 54 and 64 has a specific shape (corresponding to the specific reagent layer or the specific substrate). Accordingly, it is easy for a user to visually and tactilely discriminate between the two sensors 5 and 6.

In the following, the measuring apparatus 7 for having each of the biosensors 5 and 6 mounted therein will be described in detail.

The sensor mounting portion 70 of the measuring apparatus 7 has such a shape that the second extension portions 540 and 640 of the biosensors 6 and 7 are positioned at positions in the sensor mounting portion different from each other. Such structure of the sensor mounting portion 70 will be described below with reference to the schematic enlarged view of FIG. 5B, showing the sensor mounting portion 70 as seen in the arrow DR5 direction.

The sensor mounting portion 70 comprises faces of inlets composed of spaces D, E and F. That is, the inlet is substantially T-shaped, to which either the biosensor 5 having the second extension portion at its right side to the arrow DR5 direction or the biosensor 6 having the second extension portion at its left side to the arrow DR5 direction can be mounted in the sensor mounting portion 70, with the posture of each biosensor being so maintained that the second base plate is positioned topside thereof. More specifically, space D (its face of inlet being a rectangle defined by corner points d1, d5, d6 and d10 as shown in FIG. 5B), space E (its face of inlet being a rectangle defined by corner points d9, d6, d7 and d8 as shown in FIG. 5B) and space F (its face of inlet being rectangle defined by corner points d2, d3, d4 and d5) constitute the space of the sensor mounting portion 70.

The biosensor 5 is fitted to or corresponds to the spaces D and E of the sensor mounting portion 70, in which the second extension portion 540 of the biosensor 5 is fitted to or corresponds to the space E. On the other hand, the biosensor 6 is fitted to or corresponds to the spaces D and F of the sensor mounting portion 70, in which the second extension portion 640 of the biosensor 6 is fitted to or corresponds to the space F.

In other words, the space D is a common space (first region) to which both biosensors 5 and 6 can be fitted or can correspond. On the other hand, each of the spaces E and F is a non-common space (second region) to which only one of the biosensors (namely, only one of the second extension portions) can be fitted or can correspond. Further, the width (W3+W4 in FIG. 5B) of the space to which the second base plate 54 of the biosensor 5 is fitted is greater than the width (W3 in FIG. 5B) of the space to which the first base plate 52 is fitted. Likewise, the width (W3+W5 in FIG. 5B) of the space to which the second base plate 64 of the biosensor 6 is fitted is greater than the width (W3 in FIG. 5B) of the space to which the first base plate 62 is fitted.

Accordingly, the user cannot mount either the biosensor 5 or the biosensor 6 in the measuring apparatus in an upside down posture, namely in a top-down inverse (vertically inverse) direction. More specifically, the biosensor 5 (6) cannot be mounted in the measuring apparatus when the second base plate 54 (64) is positioned at the downside, and the first base plate 52 (62) is positioned at the topside of the biosensor. Such structure of each biosensor corresponds also to the structure of the sensor mounting portion 30 as shown by the schematic perspective view of FIG. 11.

Further, a lower part of the space D has such shape that fits or corresponds to the first extension portion 520 (620) of the biosensor 5 (6). Describing it with reference to FIG. 11, the first extension 520 (620) is fitted to or corresponds to the rectangular parallelepiped space defined by the points b1, b2, b9, b10, c1, c2, c9 and c10. Thus, it means that the lower part of the space D has such depth to an end plane defined by the points c1, c2, c9 and c10, up to which the first extension portion can be inserted.

Because of such structure, furthermore, the user cannot mount the biosensor 5 (6) in a front-rear reverse direction. More specifically, the biosensor 5 (6) cannot be mounted in the measuring apparatus when the sample solution drop deposition part 51 (61) is positioned at the front side, and the first extension portion 520 (620) is positioned at the rear side of the biosensor in the direction to the sensor mounting portion 70.

Owing to the structure of the biosensor and the sensor mounting portion of the measuring apparatus, wrong insertion or mounting of the biosensors 5 and 6 in the measuring apparatus 7 (namely, insertion in the top-down inverse direction or the front-rear reverse direction) can be securely prevented.

Hereinafter, measuring operation of the biosensor system having the biosensor 5 (6) mounted in the measuring apparatus 7 will be described with reference to FIGS. 6A, 6B, 7A, 7B, BA and 8B.

Figure 8A:
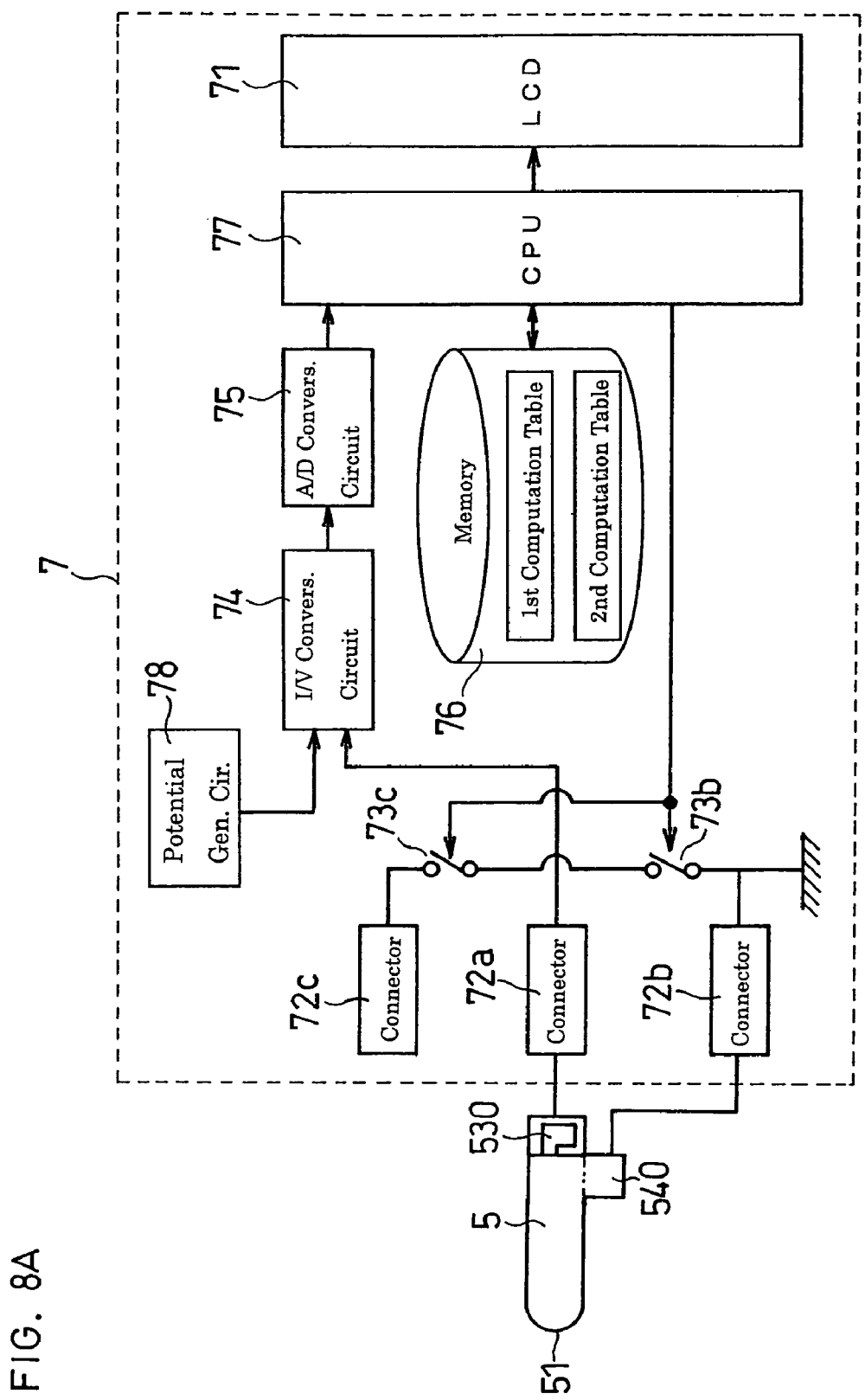
FIG. 8A is a schematic block diagram, showing an example of a connection of a biosensor to a measuring apparatus (biosensor system) according to EMBODIMENT MODE 2 of the present invention.
Figure 8B:
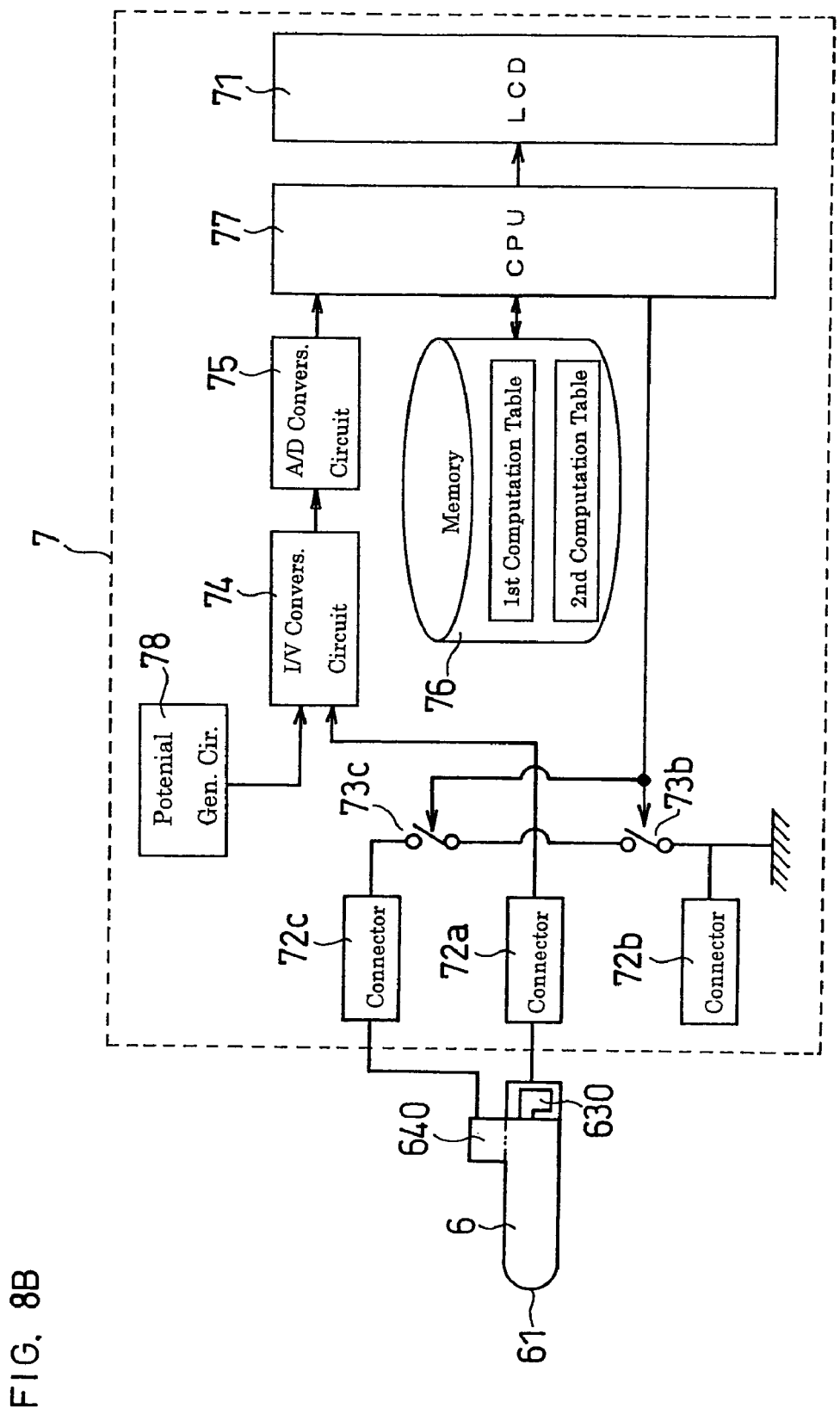
FIG. 8B is a schematic block diagram, showing a further example of a connection of a biosensor to a measuring apparatus (biosensor system) according to EMBODIMENT MODE 2 of the present invention.

FIG. 8A is a schematic block diagram showing a biosensor 5 (top plan view) and a measuring apparatus 7, while FIG. 8B is a schematic block diagram showing a biosensor 6 (top plan view) and a measuring apparatus 7.

In the measuring apparatus 7 as shown in FIG. 8A and FIG. 8B, a connector (first connection terminal) 72a is electrically connected to a lead 530 (630) provided on the first extension portion 520 (620) of the biosensor 5 (6) and exposed to outside. This connector 72a is formed at a position to contact the space D of the sensor mounting portion 70 (as shown in FIG. 5B). A connector (second connection terminal) 72b is electrically connected to a lead 550 provided on the second extension portion 540 of the biosensor 5 and exposed to outside. This connector 72b is formed at a position to contact the space E of the sensor mounting portion 70 (as shown in FIG. 5B). Further, a connector (second connection terminal) 72c is electrically connected to a lead 650 provided on the second extension portion 640 of the biosensor 6 and exposed to outside. This connector 72c is formed at a position to contact the space F of the sensor mounting portion 70 (as shown in FIG. 5B).

Further, a switch 73b is provided between the connector 72b and ground, and a switch 73c is provided between the connector 72C and ground. A potential generation circuit 78 is connected to a current-voltage (I/V) conversion circuit 74. The current-voltage conversion circuit 74 is electrically connected to the connector 72a. The value of the voltage outputted from this current-voltage conversion circuit 74 is converted to pulses by an A/D conversion circuit 75.

In the measuring apparatus, furthermore, a memory 76 is provided which has a first computation table and a second computation table. The first computation table is such table that has data showing relation between number of pulses outputted from the A/C conversion circuit 75 and glucose concentration in blood. The second computation table is such table that has data showing relation between number of pulses outputted from the A/C conversion circuit 75 and lactic acid concentration in blood.

A central processing unit (CPU) 77 conducts various operations, including on-off switching of the switches 73b and 73c, and measuring operation and computing operation on the basis of the number of pulses outputted from the A/D conversion circuit 75 and the first or the second computation table stored in the memory 76, thereby producing a calculated value corresponding to a targeted substrate in the sample solution. The calculated value is displayed on a display unit of a liquid crystal display (LCD) 71. Instead of using such display unit, it is also possible to provide a voice synthesizer as an output unit for acoustically outputting the calculated value to outside. It is also possible to output the calculated value in other ways, such as using a hard disk in an external personal computer for storing the calculated value therein, namely outputting, through a network, to outside of the measuring apparatus.

First, the case of mounting the biosensor 5 in the measuring apparatus 7 will be described with reference to FIG. 8A, FIG. 6A and FIG. 6B. When the biosensor 5 is mounted in the measuring apparatus 7, the lead 530 electrically connected to the working electrode 53 is connected to the connector 72a, while the lead 550 electrically connected to the counter electrode 55 is connected to the connector 72b.

A user deposits a drop of blood (sample solution) on the sample solution drop deposition portion 51, after the biosensor 5 is mounted in the measuring apparatus 7. The thus deposited drop of blood is sucked into the sample solution supply path 58 by capillary action. Then, a reagent layer (not shown in FIG. 8A, but shown in FIG. 6A by reference numeral 57) is dissolved in the blood, and oxidation-reduction reaction of an electron mediator in the reagent layer progresses.

More specifically, glucose oxidase, which is an enzyme carried by the reagent layer, and potassium ferricyanide, which is an electron mediator, are dissolved in the blood. Thereby, enzyme reaction between the glucose in the blood and the glucose oxidase progresses, thereby generating electrons. The potassium ferricyanide is thus reduced to potassium ferrocyanide by such generated electrons.

The measuring apparatus 7 discriminates then as to whether the mounted sensor is the biosensor 5 or the biosensor 6 in the following way. That is, the switches 73b and 73c are alternately turned on by the CPU 77, thereby alternately applying a voltage between the pair of the connectors 72a and 72b, and between the pair of the connectors 72a and 72c. Thereby, the CPU 77 detects which one of the two pairs of connectors has electric conduction therebetween.

When the pair of the connectors 72a and 73b is detected to have electric conduction therebetween, then the CPU 77 recognizes that the mounted biosensor is the biosensor 5, namely glucose sensor. On the other hand, when the pair of the connectors 72a and 73c is detected to have electric conduction therebetween, then the CPU 77 recognizes that the mounted biosensor is the biosensor 6, namely lactic acid sensor.

Since the biosensor 5 is mounted in the measuring apparatus 7 in this case, the pair of connectors 72a and 72b has electric conduction therebetween, whereby the CPU 77 recognizes that the mounted biosensor is the biosensor 5.

The CPU 77 is so designed as to turn the switch 73b on at a certain time point after the start of the measurement. Thereby, a certain potential difference (potential difference between the potential of the ground and the potential generated by the potential generation circuit 78) is generated between the working electrode 53 and the counter electrode 55 via the connectors 72a and 72b and respective leads connected to the electrodes. In other words, a certain voltage, with the potential of the counter electrode 55 being as a reference, is applied to the working electrode 53.

Then, the potassium ferrocyanide, which is a reduction product of potassium ferricyanide, is oxidized back to potassium ferricyanide, whereby an electric current flows between the working electrode 53 and the counter electrode 55 in proportion to the concentration of glucose in the blood.

In the biosensor 5, the working electrode 53 and the counter electrode 55 are opposed to each other with the sample solution supply path 58 therebetween. Accordingly, ion transfer well progresses therebetween. Thus, even when the drop of the blood to be measured is of a trace amount, an electric current proportional to the glucose concentration flows. Accordingly, the measuring apparatus 7 can be used for conducting measuring operation with high sensitivity even for a trace amount of blood.

The electric current proportional to the glucose concentration is converted to a voltage by the current-voltage conversion circuit 74. Such voltage value is further converted to pulses by the A/D conversion circuit 75, and is then fed to the CPU 77. The CPU 77 then counts the number of such pulses. Since the CPU 77 has recognized that the mounted sensor is biosensor 5 (glucose sensor), the CPU 77 selects the first computation table from the two computation tables stored in the memory 76, and conducts computation based on the first computation table, thereby calculating the glucose concentration in the blood. The calculated value is displayed on the LCD 71.

Next, the case of mounting the biosensor 6 in the measuring apparatus 7 will be described with reference to FIG. 8B, FIG. 7A and FIG. 7B. When the biosensor 6 is mounted in the measuring apparatus 7, the lead 630 electrically connected to the working electrode 63 is connected to the connector 72a, while the lead 650 electrically connected to the counter electrode 65 is connected to the connector 72c.

A user deposits a drop of blood (sample solution) on the sample solution drop deposition portion 61, after the biosensor 6 is mounted in the measuring apparatus 7. The thus deposited drop of blood is sucked into the sample solution supply path 68 by capillary action. Then, a reagent layer (not shown in FIG. 8B, but shown in FIG. 7A by reference numeral 67) is dissolved in the blood, and oxidation-reduction reaction of an electron mediator in the reagent layer progresses.

More specifically, lactic acid oxidase, which is an enzyme carried by the reagent layer, and potassium ferricyanide, which is an electron mediator, are dissolved in the blood. Thereby, enzyme reaction between the lactic acid in the blood and the lactic acid oxidase progresses, thereby generating electrons. The potassium ferricyanide is thus reduced to potassium ferrocyanide by such generated electrons.

The measuring apparatus 7 discriminates then as to whether the mounted sensor is the biosensor 5 or the biosensor 6 in the same way as described above. That is, the switches 73b and 73c are alternately turned on by the CPU 77, thereby alternately applying a voltage between the pair of the connectors 72a and 72b, and between the pair of the connectors 72*a* and 72*c*. Thereby, the CPU 77 detects which one of the two pairs of connectors has electric conduction therebetween.

Since the biosensor 6 is mounted in the measuring apparatus 7 in this case, the pair of connectors 72*a* and 72*c* has electric conduction therebetween, whereby the CPU 77 recognizes that the mounted biosensor is the biosensor 6.

The CPU 77 is so designed as to turn the switch 73*c* on at a certain time point after the start of the measurement. Thereby, a certain potential difference (potential difference between the potential of the ground and the potential generated by the potential generation circuit 78) is generated between the working electrode 63 and the counter electrode 65 via the connectors 72*a* and 72*c* and respective leads connected to the electrodes. In other words, a certain voltage, with the potential of the counter electrode 65 being as a reference, is applied to the working electrode 63.

Then, the potassium ferrocyanide, which is a reduction product of potassium ferricyanide, is oxidized back to potassium ferricyanide, whereby an electric current flows between the working electrode 63 and the counter electrode 65 in proportion to the concentration of lactic acid in the blood.

In the biosensor 6, the working electrode 63 and the counter electrode 65 are opposed to each other with the sample solution supply path 68 therebetween. Accordingly, ion transfer well progresses therebetween. Thus, even when the drop of the blood to be measured is of a trace amount, an electric current proportional to the lactic acid concentration flows. Accordingly, the measuring apparatus 7 can be used for conducting measuring operation with high sensitivity even for a trace amount of blood.

The electric current proportional to the lactic acid concentration is converted to a voltage by the current-voltage conversion circuit 74. Such voltage value is further converted to pulses by the A/D conversion circuit 75, and is then fed to the CPU 77. The CPU 77 then counts the number of such pulses. Since the CPU 77 has recognized that the mounted sensor is biosensor 6 (lactic acid sensor), the CPU 77 selects the second computation table from the two computation tables stored in the memory 76, and conducts computation based on the second computation table, thereby calculating the lactic acid concentration in the blood. The calculated value is displayed on the LCD 71.

In accordance with the arrangement of the biosensor system as described above, both glucose and lactic acid can be measured by a user, using a combination of a glucose sensor and a lactic acid sensor. This specific combination of the two biosensors can effectively be used for exercise treatment employed for treating diabetes. More specifically, a user can evaluate blood sugar level by measuring the glucose concentration in the blood, using a glucose sensor, while the user can also evaluate level of exercise load by measuring the lactic acid concentration in the blood, using a lactic acid sensor. Such system that can measure plural measurement targets by one measuring apparatus 7 is thus convenient for the user.

It is to be noted that the combination of the biosensor 5 and the biosensor 6 is not limited to such one as described above. For example, a combination of a glucose sensor and a cholesterol sensor, which is considered to be used for clinical examination, can also be skillfully used for such two biosensors (for two measurement targets) in one measuring apparatus as in the present EMBODIMENT MODE.

Further, it is also possible to so change the shapes of the first and the second base plates of the biosensor 5 (6) that the shape of the first extension portion 520 (620) is replaced by the second extension portion 540 (640). In other words, it is possible that the first base plate 52 (62) has an extension portion extending outwardly in the width direction thereof from a position corresponding to a width edge of the second base plate, and that the second base plate 54 (64) has a second extension portion extending outwardly in the length direction thereof from a position corresponding to a length edge of the first base plate. In such case, it is necessary to make the shape of the sensor mounting portion 70 of the measuring apparatus 7 correspond to the changed shape of the biosensor having such changed shapes of the two base plates.

In the above-described example, two kinds of biosensors are used. However, it is also possible to use three or more than three kinds of biosensors in one measuring apparatus, if the design of the sensor mounting portion 70 of the measuring apparatus is so changed to match up with the three or more biosensors in a manner similar to that described above, and computation tables in the memory 76 are correspondingly added.

Further, various modifications of shapes of biosensors are possible in the present EMBODIMENT MODE 2 within the concept according to the present invention in a manner similar to that described in the EMBODIMENT MODE 1, using FIG. 12 as an example.

Hereinafter, a modification of the measuring apparatus, using a sensor ejection mechanism, will be described. That is, in the measuring apparatus according to the above-described EMBODIMENT MODES 1 and 2, a sensor ejection mechanism for ejecting a biosensor once mounted in the measuring apparatus can be added in order to facilitate handy ejection thereof. An example of such sensor ejection mechanism will be described below with reference to FIG. 9 and FIGS. 10A, 10B and 10C, in which elements here similar to those already described above will be only briefly described, while the sensor ejection mechanism itself will be described in detail.

Figure 9:
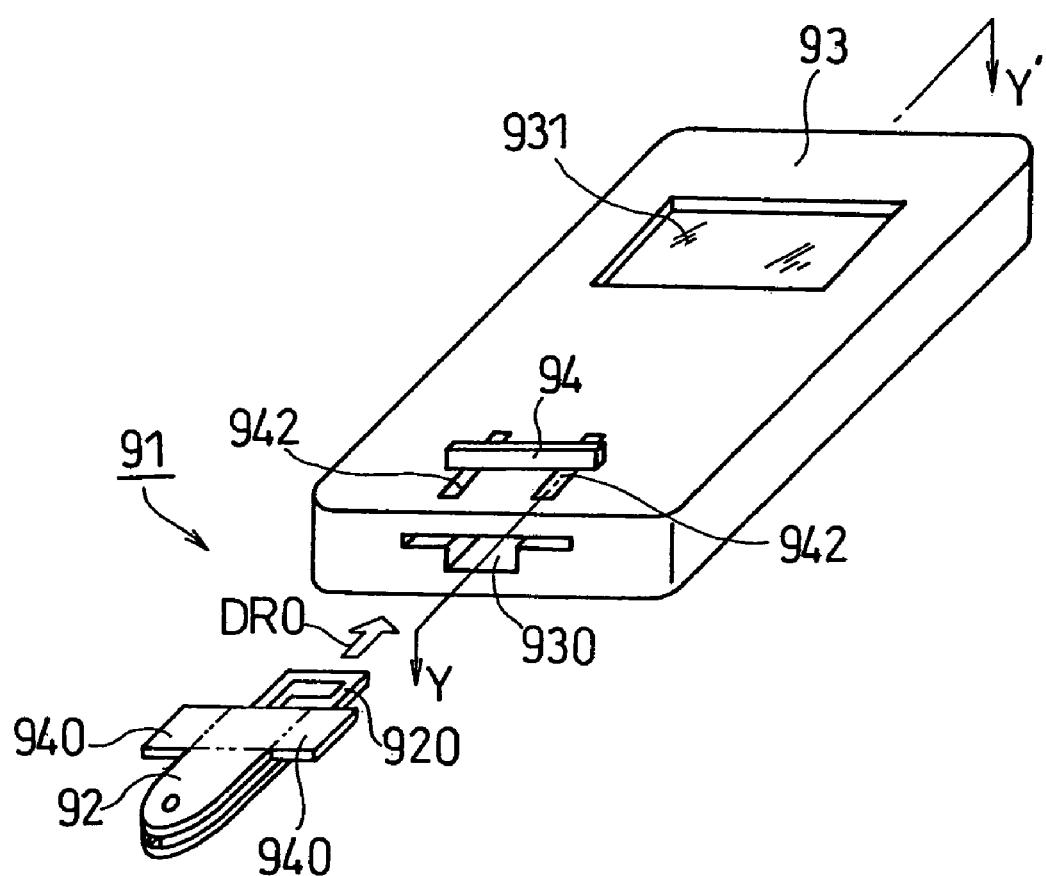
FIG. 9 is a schematic oblique view of an example of a biosensor system according to the present invention, comprising a sensor ejection mechanism for ejecting the biosensor to outside of the sensor mounting portion.

FIG. 9 is a schematic oblique view of an example of a biosensor system 91, comprising a sensor ejection mechanism for ejecting a biosensor 92 to outside of a sensor mounting portion of a measuring apparatus 93. The measuring apparatus 93 is also provided with a display unit 931.

Figure 10A:
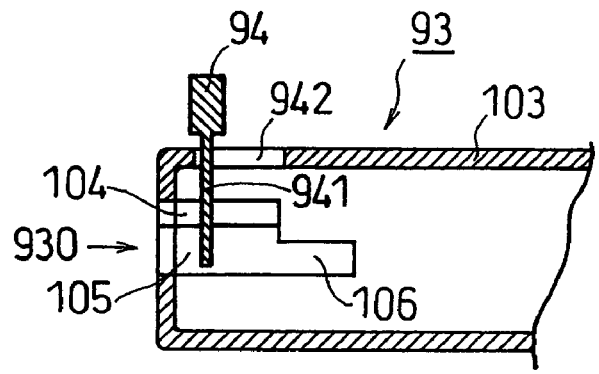
FIG. 10A is a schematic cross-sectional view of an end portion of the measuring apparatus, cut by plane Y–Y' as shown in FIG. 9.
Figure 10B:
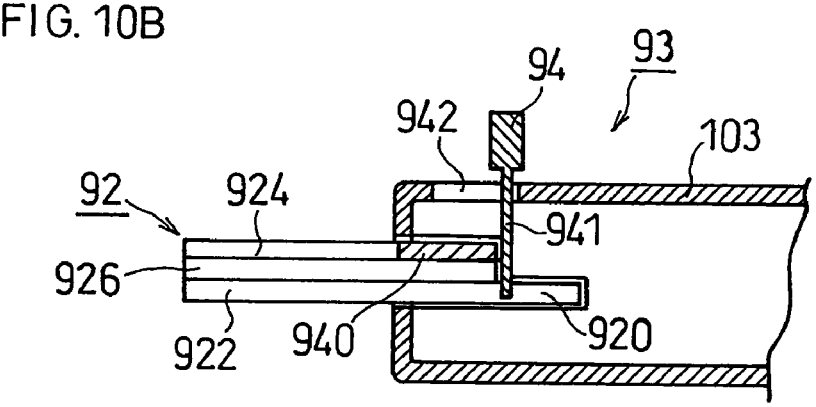
FIG. 10B is a schematic cross-sectional view of an end portion of the measuring apparatus having the biosensor mounted therein, cut by plane Y–Y' as shown in FIG. 9.
Figure 10C:
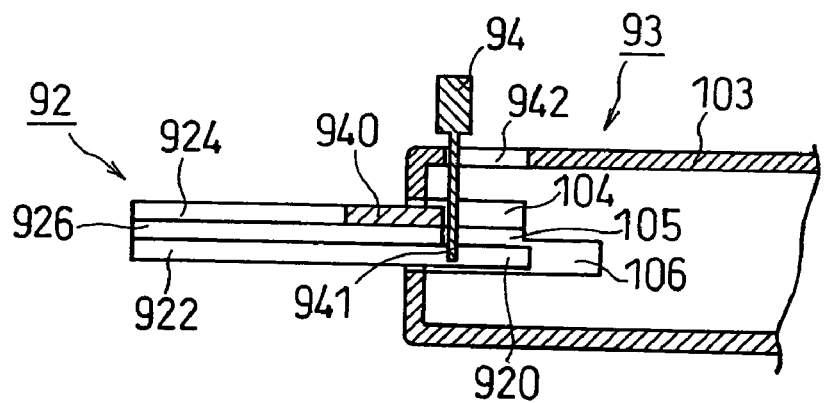
FIG. 10C is a schematic cross-sectional view, similar to that of FIG. 10B, of an end portion of the measuring apparatus having the biosensor mounted therein, in which the biosensor is pushed out, for ejection, from the sensor mounting portion of the measuring apparatus.

FIG. 10A, FIG. 10B and FIG. 10C are schematic cross-sectional views of an end portion of the measuring apparatus, mainly sensor mounting portion 930, cut by plane Y–Y' as shown in FIG. 9, in which the plane Y–Y' is vertical to top plane of a wall 103 of a housing of the measuring apparatus 93, and passes through a center of one of two slit-like openings 942 provided on the topside of the wall 103. Among them, FIGS. 10A and 10B respectively show such arrangement before and after the biosensor 92 is mounted in the sensor mounting portion 930. On the other hand, FIG. 10C shows such arrangement in which the biosensor 92 is pushed out, for ejection, from the sensor mounting portion 930.

The biosensor 92 comprises a first base plate 922 having a first extension portion 920, and a second base plate 924 having a second extension portion 940. A spacer member 926 is sandwiched between the two base plates. The biosensor 92 is inserted and mounted in the sensor mounting portion 930 in the direction shown by arrow DR0. The sensor mounting portion 930 has only a part of the biosensor 92 mounted therein, namely a portion thereof between the position shown by the dashed double-dotted line drawn on the top (second) base plate vertically to the arrow DR0 direction and the end position (closest to and facing the sensor mounting portion 930) of the biosensor in the length direction thereof.

With reference to FIGS. 10A and 10C, space 104 of the sensor mounting portion 930 corresponds to the end portion of the second base plate 924 composed of the two second extension portions 940 and of the portion between the two second extension portions 940. Space 105 corresponds to the spacer 926 and the first base plate 922. An end space 106 corresponds to the first extension portion 920 of the first base plate 922. Adding a description about these spaces with reference to FIG. 11, the space 104 corresponds to the rectangular parallelepiped space defined by the points a4, a5, a6, a7, b4, b5, b6 and b7, while the space 106 corresponds to the rectangular parallelepiped space defined by the points b1, b2, b9, b10, c1, c2, c9 and c10.

A sensor ejection member 94 is provided at the sensor mounting portion 930. The sensor ejection member 94 comprises two fingers 941 (only one of the two being shown in FIGS. 10A to 10C), which respectively extend into the spaces 104 and 105 through two slit-like openings 942. The sensor ejection member 94 is so designed as to be slidably provided at the openings 942. More specifically, the sensor ejection member 94 can be manually moved to the arrow DR0 direction or the direction opposite thereto, using a part thereof exposed to outside of the housing 103 of the measuring apparatus 93. Further, the sensor ejection member can be moved to the arrow DR0 direction, when the biosensor is inserted and mounted in the sensor mounting portion 930 to the DR0 direction.

Let it be assumed that the sensor ejection member 94 is first positioned at such position as shown in FIG. 10A. When the biosensor 92 is inserted into the sensor mounting portion 930 then, the second extension portions 940 of the biosensor 92 get in contact with the fingers 941, thereby causing abutment between the second extension portion and the finger. When the biosensor 92 is further inserted into the sensor mounting portion 930 from such abutment position, the biosensor 92 is fittedly mounted in the sensor mounting portion 930 as shown in FIG. 10B. More specifically, the fingers 941 are pushed in to the end portions of the slit-like openings, and the first extension portion 920 of the biosensor 92 becomes fitted to the space 106.

Let it be assumed that the biosensor 92 and the sensor ejection member 94 are positioned as shown in FIG. 10B. When the sensor ejection member 94 is then pushed by a user toward the end or inlet position of the measuring apparatus 93 (to the left direction in FIG. 10B), using the exposed part of the sensor ejection member 94, the biosensor 92 becomes ejected toward outside of the sensor mounting portion 930 as shown in FIG. 10C. In other words, according to the sensor ejection mechanism as shown in FIGS. 10A to 10C., push-in force and push-out force are applied to the abutment between the second extension portion of the biosensor and the finger of the sensor ejection member, namely that the second extension portion and the finger supply the push-in and push-out force to each other.

An advantage of such sensor ejection mechanism is in that the biosensor can be ejected from the sensor mounting portion to outside, and can be disposed in case of need, without making it necessary for the user to directly touch the biosensor after the measurement. This is an advantage from the viewpoint of sanitation as well.

Furthermore, such ejection mechanism can be used for a biosensor contained in a biosensor cartridge containing a plurality of biosensors (not only for a biosensor to be handled individually as exemplified above), as will be briefly described in the following. An example of biosensor cartridge is a cylindrical cartridge for having plural biosensors arranged on the surface of a cylinder in a manner that the length direction of each biosensor is parallel to the center axis of the cylinder. Another example of biosensor cartridge is a circular disk cartridge for having plural biosensors radially arranged on the surface of a disk in a manner that the center line on each biosensor in its length direction coincides with the center of the disk.

A biosensor system can be designed to have such structure and to conduct such operation as described in the following. First, such cartridge, either cylindrical or circular disk, is placed in the vicinity of the measuring apparatus in a manner that an end position of one biosensor (contained in such cartridge) in its length direction (for example, end position of the end portion of biosensor 20 in FIG. 1 facing the measuring apparatus) faces the sensor mounting portion (for example, the sensor mounting portion 30 in FIG. 1) of the measuring apparatus. The thus faced biosensor is mounted in the sensor mounting portion, and is then subjected to targeted measurement. After the measurement, the biosensor is ejected to outside of the sensor mounting portion in a manner, in case of need, that the biosensor is returned to the place where it was originally contained in the cartridge for again containing the biosensor having been subjected the measurement, or that the biosensor is simply ejected outside the measuring apparatus.

An advantage of such biosensor cartridge is that plural biosensors can be easily mounted in and ejected out of a measuring apparatus.

As described in the foregoing, the present invention provides such a biosensor and such a measuring apparatus for a biosensor that it is easy to prevent wrong insertion or mounting of the biosensor by a user in the measuring apparatus. Further, plural different biosensors can be handily measured by one measuring apparatus.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising:
 a first insulating base plate comprising a first electrode provided thereon, and a second insulating base plate comprising a second electrode provided thereon, said first and said second electrodes being opposed to each other; and
 a first lead provided on said first base plate and connected to said first electrode, and a second lead provided on said second base plate and connected to said second electrode,
 wherein said first base plate comprises a first extension portion which extends in a length direction of said first base plate from a position corresponding to an end of said second base plate in its length direction, and has at least a part of said first lead exposed to outside, and
 wherein said second base plate comprises a second extension portion which extends in a width direction of said second base plate from a position corresponding to an end of said first base plate in its width direction, and has at least a part of said second lead exposed to outside on the second extension portion.

2. The biosensor according to claim 1, wherein said second base plate comprises two of said second extension portions, one of which extends in said width direction of said second base plate from said position corresponding to said end of said first base plate in its width direction, and the other of which extends in said width direction of said second base plate from a further position corresponding to a further end of said first base plate in its width direction.

3. The biosensor according to claim 1, which further comprises:
a sample solution supply path for supplying a sample solution containing a plurality of substrates in a manner that said sample solution contacts said first electrode and said second electrode; and
a reagent which can react with at least one specific substrate in said plurality of substrates,
wherein said first base plate and said second base plate each comprises a part having a common shape and a part having a non-common shape relative to the other base plate.

4. The biosensor according to claim 3, wherein said first extension portion of said first base plate or said second extension portion of said second base plate is positioned at a specific position corresponding to said specific substrate.

5. The biosensor according to claim 4, wherein said specific position of said second extension portion of said second base plate is left position or right position, corresponding to said specific substrate, in said width direction of said second base plate.

6. The biosensor according to claim 3, wherein said plurality of substrates are glucose and lactic acid.

7. A measuring apparatus for biosensor, comprising a bisensor mounting portion for mounting the biosensor according to claim 3,
wherein said bisensor mounting portion comprises segmental portions respectively provided therein at positions corresponding to said common part and said non-common part of said first base plate or said second base plate, and
wherein when said biosensor is mounted in said bisensor mounting portion, said specific substrate in said biosensor is discriminated by the position of said segmental portion of said sensor mounting portion corresponding to said non-common part of said first base plate or said second base plate.

8. The measuring apparatus according to claim 7, wherein said sensor mounting portion comprises an integral fitting space for having said sensor fitted thereto, which space comprises:
a first tee ion corresponding to said common part of said shape of said first base plate or said second base plate; and
a second region corresponding to said non-common part of said shape of said first base plate or said second base plate.

9. The measuring apparatus according to claim 8, which further comprises:
a first electric connection terminal positioned therein for contact with said first region of said integral fitting space; and
a plurality of second electric connection terminals positioned therein for contact with said second region of said integral fitting space,
wherein when said biosensor is mounted in said sensor mounting portion, one of said first and said second leads is connected to said first electric connection terminal, and the other of said first and said second leads is connected to one of said plurality of second electric connection terminals, and
wherein said specific substrate in said biosensor is discriminated by said one of said plurality of second electric connection terminals to which said other of said first and said second leads is connected.

10. A measuring apparatus for biosensor, comprising a sensor mounting opening section for mounting therein a biosensor comprising a first base plate and a second base plate, wherein said sensor mounting opening comprises:
a first sensor mounting segmental portion corresponding to said first base plate of said biosensor; and
a second sensor mounting segmental portion corresponding to said second base plate of said biosensor, and wherein said first sensor mounting segmental portion has a width different from that of said second sensor mounting segmental portion; and wherein said first base plate of said biosensor comprises a first electrode and a first lead provided thereon, said first lead being connected to said first electrode; said second base plate comprises a second electrode and a second lead provided thereon, said second lead being connected to said second electrode; and said first and said second electrodes are opposed to each other, wherein said first base plate comprises a first extension portion which extends in a length direction of said first base plate from a position corresponding to an end of said second base plate in its length direction, and has at least a part of said first lead exposed to outside, and wherein said second base plate comprises a second extension portion which extends in a width direction of said second base plate from a position corresponding to an end of said first base plate in its width direction, and has at least a part of said second lead exposed to outside on the second extension portion.

11. The measuring apparatus according to claim 10, which further comprises:
a first electric connection terminal to be connected with said exposed part of said first lead, and a second electric connection terminal to be connected with said exposed part of said second lead of said biosensor when said biosensor is mounted in said sensor mounting portion; and
a driving power supply coupled to said first and said second electric connection terminals for applying a voltage to said first and said second electrodes of said biosensor through said first and said second electric connection terminals.

12. The measuring apparatus according to claim 11, which further comprises:
a signal processor to be operatively coupled to said first electrode and said second electrode of said biosensor for processing computation using a value of electric current flowing in said first electrode and said second electrode, thereby generating a calculated value; and
an output unit operatively coupled to said signal processor for outputting said calculated value by said computation of said signal processor, whereby when said biosensor is provided with a sample solution containing a substrate, and is mounted in said sensor mounting portion, the amount of said substrate is calculated by said computation processing of said signal processor, and said calculated value is outputted to said outputting unit.

13. The measuring apparatus according to claim 10, which further comprises a sensor ejection member provided at said sensor mounting portion for ejecting said biosensor to outside of said sensor mounting portion in a manner that said biosensor is provided with a push-out force by said ejection member.

14. The measuring apparatus according to claim 13, wherein said push-out force by said ejection member is provided to abutment between said ejection member and said second extension portion of said biosensor.

* * * * *

UNITED STATES PATENT AND TRADEMARK OFFICE
CERTIFICATE OF CORRECTION

PATENT NO. : 6,969,450 B2 Page 1 of 1
APPLICATION NO. : 10/616305
DATED : November 29, 2005
INVENTOR(S) : Yuko Taniike et al.

It is certified that error appears in the above-identified patent and that said Letters Patent is hereby corrected as shown below:

IN THE CLAIMS,
Column 29, line 52, change the phrase "a first tee ion corresponding" to -- a first region corresponding --.

Signed and Sealed this

Thirty-first Day of October, 2006

JON W. DUDAS
*Director of the United States Patent and Trademark Office*